(12) United States Patent
Konno

(10) Patent No.: US 8,535,218 B2
(45) Date of Patent: Sep. 17, 2013

(54) CAPSULE ENDOSCOPE

(75) Inventor: Mitsujiro Konno, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1898 days.

(21) Appl. No.: 11/407,917

(22) Filed: Apr. 21, 2006

(65) Prior Publication Data

US 2006/0238614 A1    Oct. 26, 2006

(30) Foreign Application Priority Data

Apr. 26, 2005    (JP) ................................. 2005-128250

(51) Int. Cl.
*A61B 1/04* (2006.01)
*A61B 1/06* (2006.01)

(52) U.S. Cl.
USPC .......................................... 600/109; 600/160

(58) Field of Classification Search
USPC ........................... 600/103, 109, 117, 118, 160
See application file for complete search history.

(56) References Cited

U.S. PATENT DOCUMENTS

| 6,939,295 | B2 | 9/2005 | Yokoi et al. | |
|---|---|---|---|---|
| 2002/0109774 | A1* | 8/2002 | Meron et al. | 348/74 |
| 2003/0158503 | A1* | 8/2003 | Matsumoto | 600/593 |
| 2003/0181788 | A1* | 9/2003 | Yokoi et al. | 600/160 |
| 2003/0208107 | A1* | 11/2003 | Refael | 600/300 |
| 2004/0092825 | A1* | 5/2004 | Madar et al. | 600/473 |
| 2005/0004474 | A1* | 1/2005 | Iddan | 600/476 |
| 2006/0004255 | A1* | 1/2006 | Iddan et al. | 600/160 |

FOREIGN PATENT DOCUMENTS

| JP | 2003-038425 A | 2/2003 |
|---|---|---|
| JP | 2003-070728 A | 3/2003 |
| JP | 2003-275171 A | 9/2003 |
| WO | WO 02/054932 A2 | 1/2002 |
| WO | WO 02/054932 | 7/2002 |
| WO | WO 03/003706 | 1/2003 |

* cited by examiner

*Primary Examiner* — Philip R Smith
(74) *Attorney, Agent, or Firm* — Arnold International; Jon W. Henry; Bruce Y. Arnold

(57) ABSTRACT

A capsule endoscope is disclosed that includes first and second objective optical systems for forming images of objects viewed in the capsule insertion direction and in the opposite direction on separate areas of one plane where an image pickup surface of an image pickup device is located. The capsule endoscope also includes illuminators for illuminating the objects, and a deflector or deflectors, such as reflecting prisms, for folding light from the objective optical systems to the image pickup surface so that the image pickup surface is parallel to the capsule insertion direction. The objective optical systems are retrofocus optical systems. The illuminators may have emission surfaces centered on the centers of spheres defined by dome-shaped transparent covers aligned along a central axis of the capsule endoscope. The objective optical systems, the deflector or deflectors, and the image pickup device are arranged completely off the central axis of the capsule endoscope.

8 Claims, 23 Drawing Sheets

CAPSULE ENDOSCOPE

CROSS REFERENCE TO RELATED APPLICATION

The present application claims benefit of priority under 35 U.S.C. §119 of JP 2005-128,250, filed Apr. 26, 2005, the contents of which are hereby incorporated by reference.

TECHNICAL FIELD OF THE INVENTION

The present invention relates to a capsule endoscope for in vivo examination, particularly to a capsule endoscope that allows for observation of an image of an object in the capsule insertion direction and allows for observation of an image of an object in the direction opposite to the capsule insertion direction.

BACKGROUND OF THE INVENTION

Recently, capsule endoscopes have been increasingly used for making diagnoses of digestive organs in living bodies. Known prior art capsule endoscopes for these diagnoses are described in, for example, U.S. Pat. No. 6,939,295 and in International Patent Publication WO 02/054932A2.

FIG. 21 shows an exemplary structure of a prior art capsule endoscope described in U.S. Pat. No. 6,939,295, and FIG. 22 shows an exemplary structure of a prior art capsule endoscope described in International Patent Publication WO 02/054932A2. In the capsule endoscope having the structure shown in FIG. 21, an objective optical system 52 faces a dome-shaped transparent cover 51, an image pickup device 53 such as a CMOS is provided at the imaging position of the objective optical system 52, and light sources 54, 54 such as white LEDs, are provided around the objective optical system 52.

The image pickup device 53 is connected to a drive and processing circuit 55. The drive and processing circuit 55 includes a DSP (digital signal processor) circuit for converting analog signals from the image pickup device 53 to digital signals and a light modulation circuit for changing the brightness of the light sources 54, 54 according to image information. A circuit board that includes a memory circuit 56 for storing image data is arranged behind a circuit board that includes the drive and processing circuit 55.

A circuit board that includes a wireless communication circuit 57 is arranged behind the circuit board that includes the memory circuit 56. Additionally, two button-type batteries 58, 58 are provided behind the circuit board that includes the wireless communication circuit 57. An antenna 59 that is connected to the wireless communication circuit 57 is provided within the capsule endoscope.

After being swallowed, the capsule endoscope having the structure described above proceeds within the digestive tract of the person undergoing examination while emitting light from the light source 54 in order to illuminate a site in front of the capsule endoscope and to form an image of the illuminated site. An image of such a site, termed herein an 'observation target site', is formed on the image pickup surface of the image pickup device 53 by the objective optical system 52. The observation target site image captured by the image pickup device 53 is digitally processed by the drive and processing circuit 55 and the digitally processed image data is stored by the memory circuit 56. The stored image data is then transmitted by the wireless communication circuit 57 via the antenna 59 to an external antenna (not shown in the drawings) and displayed on a display system (not shown in the drawings).

When inserted into the body, a capsule endoscope causes significantly less pain to a patient during in vivo examination as compared with the pain caused by inserting a prior art endoscope having a tubular insertion part.

Recently, it has been noticed that examining the junction between the esophagus and the stomach for "Barrett's esophagus" is important for the early detection of esophageal cancer and/or for the detection of a lesion before it becomes cancerous. "Barrett's esophagus" is a syndrome in which mucosal tissue similar to the gastric mucosa develops in the esophagus after stomach acid refluxes into the esophagus and this process continues over a prolonged period of time. When the tissue of the esophagus has deteriorated to the point of "Barrett's esophagus," the tissue of the esophagus is very likely to turn cancerous. Therefore, "Barrett's esophagus" is considered to be a pre-cancerous condition.

In order to improve the accuracy of the diagnosis of "Barrett's esophagus," it is important to observe the tissue around the junction between the esophagus and the stomach, both from the esophagus side and from the stomach side, so that any lesion present will not be overlooked.

The prior art capsule endoscope disclosed in U.S. Pat. No. 6,939,295 provides for observation only in one direction, that is, in the direction of travel through the body. It is not constructed for observation in two opposite directions, forward and backward, along the traveling direction. Therefore, the capsule endoscope disclosed in U.S. Pat. No. 6,939,295 is not capable of a highly accurate diagnosis of "Barrett's esophagus."

On the other hand, the capsule endoscope described in International Patent Publication WO 02/054932A2 includes illumination systems 61, 61', objective optical systems 62, 62', image pickup devices 63, 63' (such as CCDs) arranged in dome-shaped transparent covers 60, 60' at both ends of the capsule, respectively, so that observations can be made of images of observation target sites in both the forward and backward directions along the travel path. These structures are arranged in the capsule endoscope, along with batteries 64, 64, an antenna 65, and a transmitter 66.

However, when two image pickup devices are provided as in the capsule endoscope described in International Patent Publication WO 02/054932A2, the following problems occur. First, a significant amount of power is required to drive a solid state image pickup element that forms an image pickup device such as a CCD. When two CCDs are provided, the driving power is doubled, requiring a large battery within the capsule endoscope. Additionally, each CCD requires a drive circuit, inevitably increasing the capsule size in order to provide for a space in which to house the required structures.

In addition, the capsule endoscope passes through the esophagus at a relatively high speed for making observations. In order to minimize the chance of overlooking a lesion, an observation image should be acquired at each observation point in as short a time as possible. In other words, the image pickup device must have a high frame rate. The observation image acquisition time of a capsule endoscope is determined by the time required for the image pickup device to capture an image and the time required for the image to be wirelessly transmitted. Hence, when two image pickup devices are provided in a capsule endoscope, at least the following steps are involved: (1) capturing an image by one of the image pickup devices; (2) transferring the captured image data to the outside of the capsule endoscope by the communication device; (3) capturing an image by the other image pickup device; and (4) transferring the captured image data to the outside of the capsule endoscope by the communication device. Therefore, the observation image acquisition time is doubled in comparison with the prior art observation capsule endoscope described in U.S. Pat. No. 6,939,295 that observes in only one direction. Consequently, the capsule endoscope described in International Patent Publication WO 02/054932A2 proceeds twice the distance within the esophagus before the next observation image in a given viewing direction is captured. Thus, the prior art capsule endoscope having two image pickup devices may fail to prevent "Barrett's esophagus" from being overlooked.

BRIEF SUMMARY OF THE INVENTION

The present invention relates to a small capsule endoscope that allows for observation of an image of an object in the capsule insertion direction and an image of an object in the direction opposite to the capsule insertion direction using an image pickup device that has a high frame rate, and that can enable highly accurate diagnoses of conditions such as "Barrett's esophagus".

DETAILED DESCRIPTION

Figure 1:
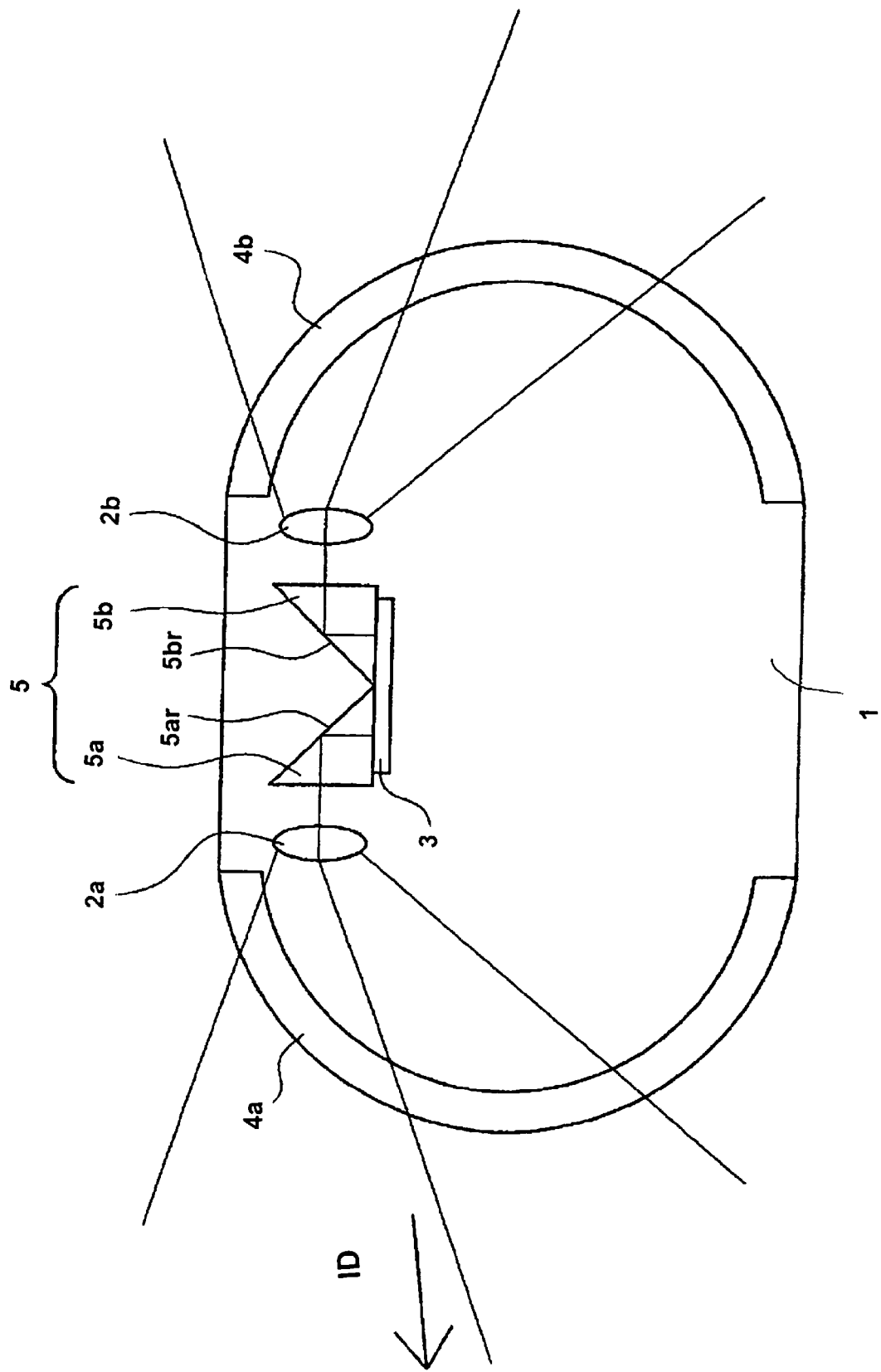
FIG. 1 illustrates the basic optical and imaging structures of the present invention.
Figure 2:
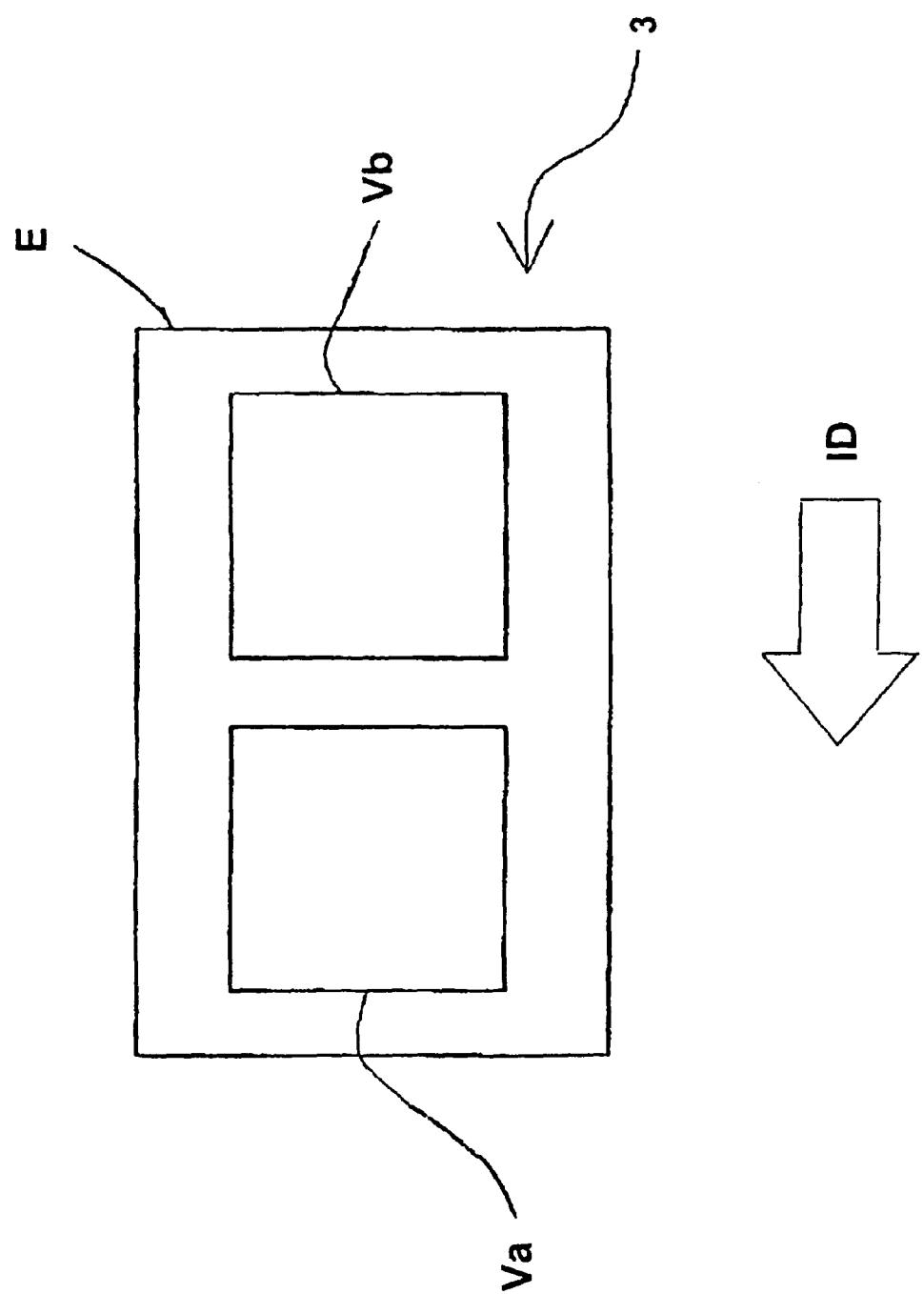
FIG. 2 illustrates the positional relationship between the image pickup area where an image of an object in the capsule insertion direction is captured and the image pickup area where an image of an object in the direction opposite to the capsule insertion direction is captured on the effective image pickup area of an image pickup device in the capsule endoscope of the present invention.
Figure 3:
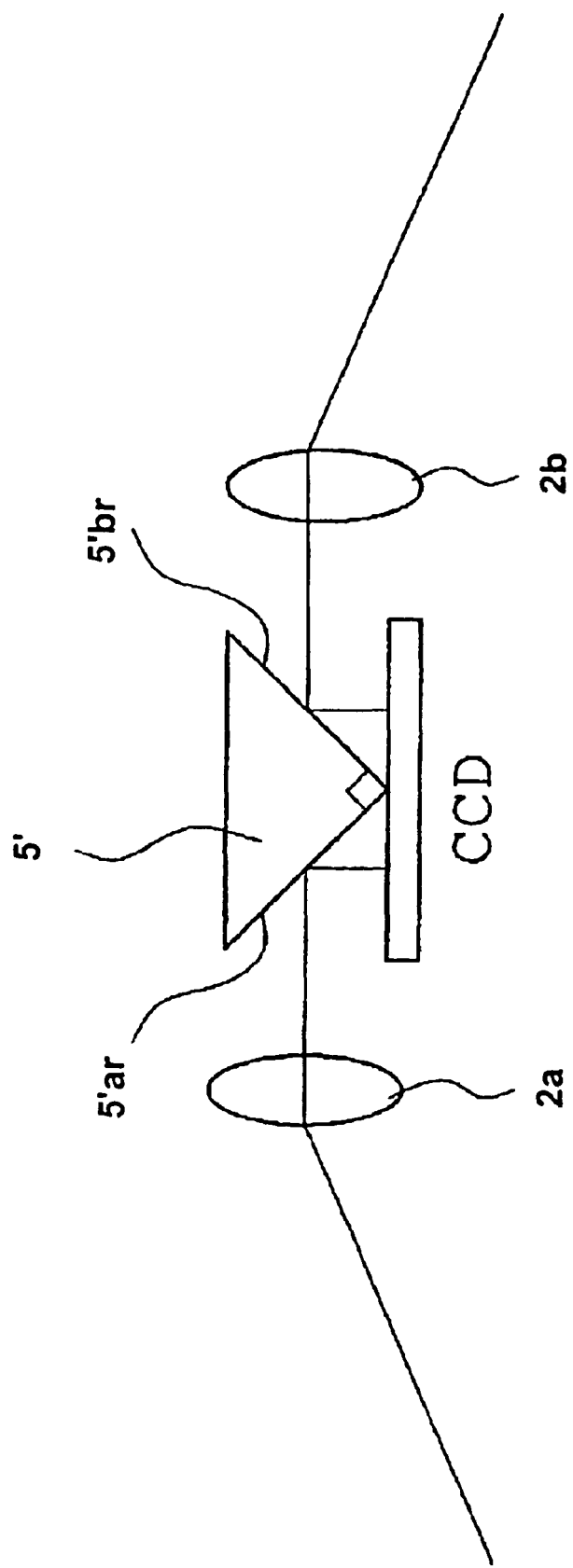
FIG. 3 illustrates a modification of a deflector of the capsule endoscope of the present invention.

FIG. 1 illustrates the basic optical and imaging structures of the present invention. FIG. 2 illustrates the positional relationship between the image pickup area where an image of an object in the capsule insertion direction ID is captured and the image pickup area where an image of an object in the direction opposite to the capsule insertion direction is captured on the effective image pickup area of an image pickup device in the capsule endoscope of the present invention. FIG. 3 illustrates a modification of the deflector of the capsule endoscope of the present invention.

With reference to FIG. 1, in the present invention, a capsule endoscope 1 includes: two illuminators (not illustrated in FIG. 1) for illuminating in two directions (i.e., the capsule insertion direction ID illustrated by a horizontal arrow directed to the left in FIG. 1, and the direction opposite to the capsule insertion direction); two objective optical systems 2a and 2b that form images of two observation target sites illuminated by the two illuminators; an image pickup device 3 that captures the observation target site images formed by the objective optical systems 2a and 2b; and two dome-shaped transparent covers 4a and 4b, one at each end of the capsule endoscope that covers a respective illuminator and the respective objective optical system 2a or 2b.

One of the two illuminators, the objective optical system 2a, and the transparent cover 4a are arranged in the capsule insertion direction ID defining the direction of endoscope insertion. The other illuminator, the objective optical system 2b, and the transparent cover 4b are arranged in the direction opposite to the capsule insertion direction.

The objective optical systems 2a and 2b form an image of an observation target site in the capsule insertion direction and an image of an observation target site in the direction opposite to the capsule insertion direction, respectively, on the image pickup surface of the image pickup device 3 in different image pickup areas Va and Vb, respectively, illustrated in FIG. 2. The image pickup device 3 has an effective image pickup area E, illustrated in FIG. 2, that is sufficient for acquiring VGA (Video Graphic Array) images or higher resolution images. The image pickup areas Va and Vb on the effective image pickup area each have an area sufficient for acquiring a CIF (Common Intermediate Format) image or equivalent image. The image pickup device 3 is placed with the image pickup surface parallel to the capsule insertion direction ID.

The capsule endoscope 1 of the present invention may further include a deflector 5 that includes two reflecting prisms 5a and 5b for reflecting imaging light beams from the two objective optical systems 2a and 2b to the image pickup device 3, as shown in FIG. 1, particularly to the different image pickup areas Va and Vb, respectively, on the image pickup surface of the image pickup device 3, as shown in FIG. 2.

As shown in FIG. 1, the reflecting prisms 5a and 5b are right angle prisms that include reflecting surfaces 5ar and 5br, respectively, on the hypotenuses of the right angle prisms. The reflecting prisms are arranged between the objective optical systems 2a and 2b and the image pickup areas Va and Vb, respectively, (FIG. 2) so as to fold the optical axes of the objective optical systems 2a and 2b at right angles so that the optical axes intersect the image pickup areas Va and Vb at the center of each image pickup area, respectively. More generally, it is preferable that the optical axes of the objective optical systems 2a and 2b be deflected toward the image pickup surface of the image pickup device 3 by the reflecting prisms so that the following Condition is satisfied:

$$|Tw| \geqq 60°$$ Condition (1)

where

Tw is the angle between the optical axis of the objective optical system and the image pickup surface of the image pickup device.

If Condition (1) above is not satisfied, light enters the image pickup surface of the image pickup device primarily obliquely, which causes the image quality to deteriorate, particularly at the periphery of the image. Additionally, if Condition (1) is not satisfied, manufacturing the prism becomes difficult. More desirably, the following Condition is satisfied:

$$|Tw| \geqq 75°$$ Condition (2)

where

Tw is defined as set forth previously.

The reflecting prisms can be prisms that do not have a right angle vertices as long as they deflect the optical axes of the objective optical systems 2a and 2b relative to the image pickup surface of the image pickup device 3 in the manner explained above with regard to satisfying Conditions (1) and/or (2) above. Additionally, the reflecting prisms can be arranged in the middle of the objective optical systems 2a and 2b.

In FIG. 1, the deflector 5 includes two reflecting prisms, each having a single reflecting surface. However, as shown in FIG. 3, a deflector 5' that includes a single reflecting prism having two reflecting surfaces can be used for both objective optical systems 2a and 2b. In this case, the deflector 5' has reflecting surfaces on two surfaces 5'ar and 5'br that form a right angle vertex. The reflecting surfaces fold the optical axes of the objective optical systems 2a and 2b so that the optical axes intersect the image pickup areas Va and Vb at their centers, respectively. The deflector 5' can be a prism with other than a right angle vertex as long as it has reflecting surfaces that fold the optical axes of the objective optical systems 2a and 2b toward the image pickup surface of the image pickup device 3 at nearly right angles.

In the capsule endoscope of the FIG. 1, light from an observation target site in the capsule insertion direction (hereinafter termed "front") forms an image on the image pickup area Va of the image pickup device 3 via the transparent cover 4a, the objective optical system 2a, and reflecting prism 5a. Meanwhile, light from an observation target site in the direction opposite to the capsule insertion direction (hereinafter termed "back") forms an image on the image pickup area Vb of the image pickup device 3 via the transparent cover 4b, the objective optical system 2b, and reflecting prism 5b. The two images are formed as two image surfaces that are in, or very nearly in, the same plane. Additionally, the image pickup device 3 captures the two images on an image pickup surface that is situated at, or very nearly at, both image surfaces.

In the capsule endoscope of the present invention, an image of the front observation target site (hereinafter termed "front image") and an image of the back observation target site (hereinafter termed "back image") are simultaneously captured by a single image pickup device. Using a single image pickup device saves power for driving the image pickup device. Also, the battery space and the drive circuit can be reduced in size, which enables the outer diameter of the capsule endoscope to be decreased. In addition, the image pickup device can have a higher frame rate, as described in detail below.

Figures 4A, 4B:
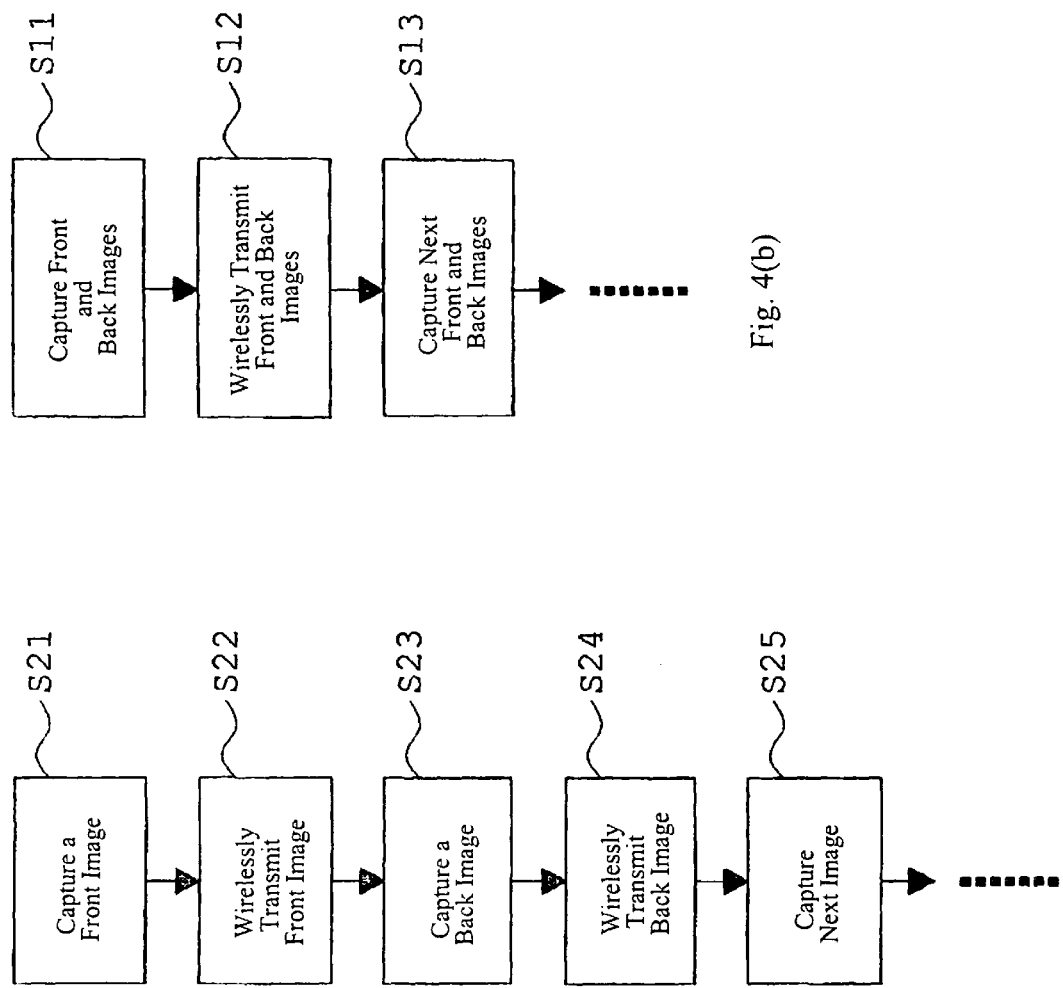
FIGS. 4(a) and 4(b) are flowcharts for explaining the difference between the present invention and the prior art, with FIG. 4(a) being a flowchart of the process of the prior art capsule endoscope from capturing an image to transmitting image data to the outside of the capsule endoscope, and FIG. 4(b) being a flowchart of the process of the capsule endoscope of the present invention from capturing an image to transmitting image data to the outside of the capsule endoscope.

FIGS. 4(a) and 4(b) are flowcharts for explaining the difference between the present invention and the prior art, with FIG. 4(a) being a flowchart of the process of the prior art capsule endoscope from capturing an image to transmitting image data to the outside of the capsule endoscope, and FIG. 4(b) being a flowchart of the process of the capsule endoscope of the present invention from capturing an image to transmitting image data to the outside of the capsule endoscope. These figures help explain the difference in frame rate between the capsule endoscope of the present invention and a prior art capsule endoscope having two image pickup devices.

For example, when two image pickup devices are provided as in the capsule endoscope described in International Patent Publication WO 02/054932A2, described above, images are captured (S21, S23) and wirelessly transmitted (S22, S24) separately for the front and back observation target sites before a next image is captured (S25), as indicated in FIG. 4(a).

On the other hand, in the capsule endoscope of the present invention, front and back images are simultaneously captured (S11) and wirelessly transmitted (S12), as shown in FIG. 4(b). The capsule endoscope of the present invention has only one step after capturing one front image and before capturing another front image (S13) while the prior art capsule endoscope has three steps. Therefore, the capsule endoscope of the present invention can acquire more images in one and the same direction in a given length of time. In other words, the capsule endoscope of the present invention allows the image pickup device to have a higher frame rate than the similar prior art capsule endoscope.

As described above, the capsule endoscope passes through the esophagus at a relatively high speed for making observations. The accuracy of diagnosis of "Barrett's esophagus"

should be significantly improved by capturing as many images of a lesion as possible while the capsule endoscope is moving toward and away from the lesion. The capsule endoscope of the present invention captures the front and back images and allows the image pickup device to have a higher frame rate, thereby significantly improving the accuracy of diagnosis of "Barrett's esophagus" in comparison with the similar prior art endoscope.

When a single image pickup device is used to simultaneously capture two images, as in the present invention, it is desirable that the image pickup areas Va and Vb contain as many pixels as possible so as to ensure that each image is obtained in the quality required for the diagnosis. To do so, the image pickup device must have a larger effective image pickup area. The effective image pickup area is preferably rectangular so that the image pickup areas Va and Vb can be juxtaposed on the image pickup surface. In the capsule endoscope of the present invention, the image pickup device is placed with the image pickup surface parallel to the capsule insertion direction. This enables an image pickup device of a desired size to be placed in the capsule without increasing the outer diameter of the capsule.

Figure 5:
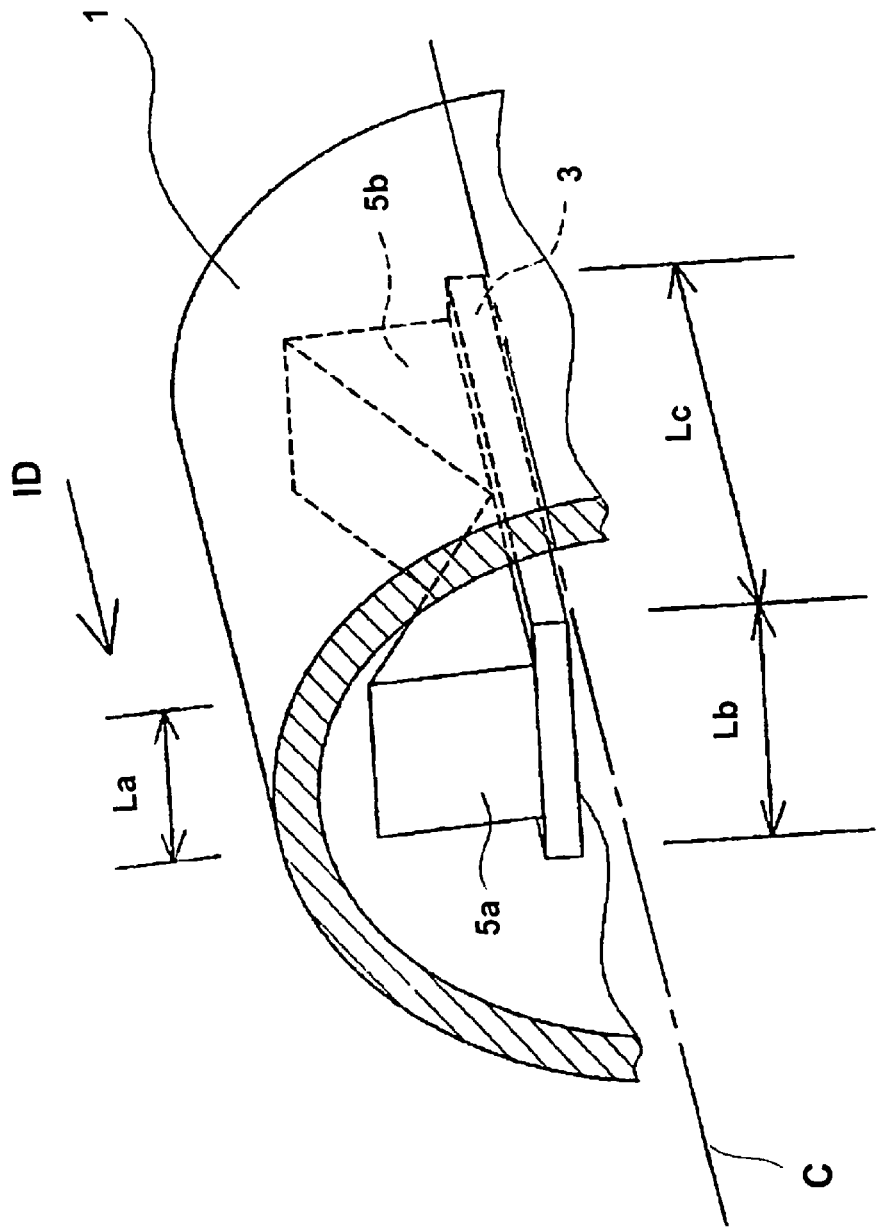
FIG. 5 illustrates the position of the image pickup device in the capsule endoscope of the present invention.

FIG. 5 illustrates the position of the image pickup device in the capsule endoscope of the present invention. As illustrated in FIG. 5, the image pickup device 3 of the capsule endoscope of the present invention has an image pickup surface that is in the shape of a rectangle having sides Lb and Lc, thus providing an effective image pickup area that is also in the shape of a rectangle.

The image pickup device 3 is arranged within the capsule endoscope so that the longer side of the rectangle is in the capsule insertion direction ID and the following Condition is satisfied:

$$La < Lb < Lc \qquad \text{Condition (3)}$$

where
La is the width, as measured in a direction parallel to Lb, of the entrance surface of each of the reflecting prisms 5a and 5b that receive light from respective objective optical systems;
Lb is the length of the shorter side of the rectangle defined by the image pickup surface; and
Lc is the length of the longer side of the rectangle defined by the image pickup surface.

Additionally, the objective optical systems (not illustrated in FIG. 5), the reflecting prisms 5a and 5b, and the image pickup device 3 are placed completely off the central axis C of the capsule endoscope.

Figure 6:
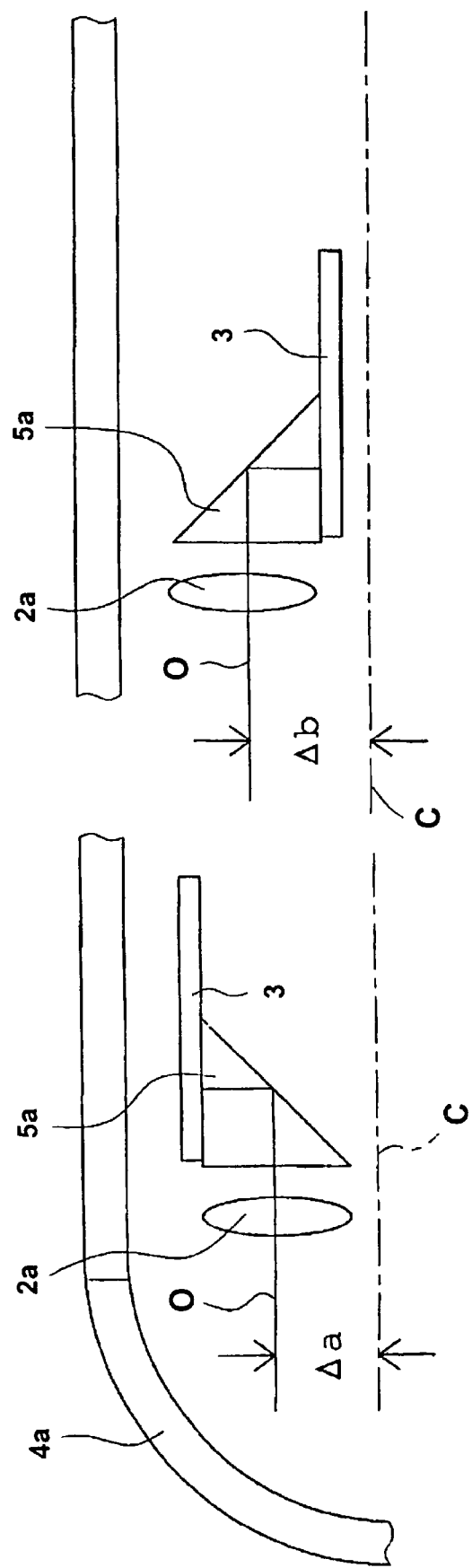
FIGS. 6(a) and 6(b) illustrate exemplary positions of the image pickup device in the capsule endoscope of the present invention, with FIG. 6(a) illustrating the image pickup device placed with the image pickup surface facing the outside of the capsule endoscope, and FIG. 6(b) illustrating the image pickup device placed with the image pickup surface facing the central axis of the capsule endoscope.

FIGS. 6(a) and 6(b) illustrate exemplary positions of the image pickup device in the capsule endoscope of the present invention, with FIG. 6(a) illustrating the image pickup device placed with the image pickup surface facing the outside of the capsule endoscope, and FIG. 6(b) illustrating the image pickup device placed with the image pickup surface facing the central axis of the capsule endoscope.

As illustrated in FIGS. 6(a) and 6(b), in the capsule endoscope of the present invention, the image pickup device 3 can be placed either with the image pickup surface facing the outside of the capsule endoscope or with the image pickup surface facing the central axis of the capsule endoscope. When the image pickup device 3 is placed with the image pickup surface facing the outside of the capsule, the image pickup device 3 is placed closer to the central axis C of the capsule endoscope, which preferably facilitates the connection to image processing, memory, and communication circuits that are provided in the space on the other side of the central axis C of the capsule endoscope near the image pickup device 3 by allowing for effective use of the internal space of the capsule endoscope.

When the image pickup device 3 is placed with the image pickup surface facing the central axis C of the capsule endoscope, that is, so that the image pickup surface receives image forming light traveling in a direction away from the central axis C, the objective optical system 2a or 2b is placed near the central axis C of the capsule endoscope. The distance Aa between the optical axis O of the objective optical system 2a and the central axis C of the capsule endoscope in the structure shown in FIG. 6(b) is smaller than the distance Ab between the optical axis O of the objective optical system 2a and the central axis C of the capsule endoscope in the structure shown in FIG. 6(a). Therefore, a desired field of view can be ensured without giving the objective optical system 2a a complicated structure, such as tilting the objective optical system relative to the central axis of the capsule endoscope so that the optical axis of the objective optical system is oriented toward an object.

In the capsule endoscope of the present invention, the optical system for acquiring the front image and the optical system for acquiring the back image can have different optical properties so as to improve the accuracy of diagnosis of "Barrett's esophagus." The observation target sites in the capsule insertion direction and in the opposite direction are different in viewing conditions such as size and brightness. Therefore, it is preferable that the optical systems each have optical properties suitable for their observation conditions. For example, the optical system for acquiring the front image preferably has optical properties based on the following considerations. In acquiring the front image, the capsule endoscope gradually approaches the observation target site and, in the vicinity of the near point of the depth of field of the optical system for acquiring the front image, the observation target site is in contact or nearly in contact with the outer surface of the transparent cover, for example, by being pressed against the outer surface of the transparent cover. For closely examining the observation target site, it is desirable that the optical system for acquiring front images have the highest resolution around the outer surface of the transparent cover. In particular, it is desirable that the optical system for acquiring the front image have a resolution of 5 lines/mm or higher for an object distance A1 (not illustrated) measured between the outermost surface of the optical system and the point where the optical axis of the optical system intersects the outer surface of the transparent cover and a resolution of 1 line/mm or higher for an object distance B1 (not illustrated) measured between the outermost surface of the optical system and the far point of the depth of field of the optical system.

The resolution of an image pickup unit is defined generally as follows. A pair of black and white lines is placed in front of the objective optical system so that an image of horizontal black and white lines is formed on the image pickup surface of a solid state image pickup element, and the image is captured by the image pickup unit and displayed on a monitor via an electrical circuit system that processes image signals sent from the solid state image pickup element. In this case, the contrast I of the black and white lines on the monitor is determined by using the following Equation (A):

$$I = (I\max - I\min)/(I\max + I\min) \qquad \text{Equation (A)}$$

where
Imax is the maximum value in the black/white intensity profile obtained in the horizontal direction on the monitor; and Imin is the minimum value in the black/white intensity profile obtained in the horizontal direction on the monitor.

The resolution is defined as the reciprocal of a width of a pair of black and white lines when the contrast 1 is 10%. "A resolution of 5 lines/mm or higher" means that a pair of black and white lines having a width of 0.2 mm or smaller exhibits a contrast of 10% or higher on the monitor and "a resolution of 1 line/mm or higher" means that a pair of black and white lines having a width of 1 mm or smaller exhibits a contrast of 10% or higher on the monitor. When the image pickup unit has a resolution of 5 lines/mm or higher for the object distance A1, the image of the living tissue near the outer surface of the transparent cover can be enlarged for observation. When the image pickup unit has a resolution of 1 line/mm or higher for the object distance B1, the observation target site is easily found at the far point of the depth of field of the optical system for acquiring the front image.

It is desirable that the optical system for acquiring the front image satisfies the following Conditions:

$$80 < IH/P < 500 \quad \text{Condition (4)}$$

$$80 < FL/P < 500 \quad \text{Condition (5)}$$

$$400 < Fno/P < 3000 \quad \text{Condition (6)}$$

where

IH is an image height, in mm, in the image pickup area of the image pickup element;

P is the pixel pitch, in mm, in the horizontal direction of the image pickup element;

FL is the focal length, in mm, of the objective optical system; and

Fno is the effective f-number of the objective optical system.

When the upper limit of Condition (4) above is not satisfied, a large depth of field cannot be obtained. On the other hand, when the lower limit of Condition (4) above is not satisfied, there is insufficient resolution in the vicinity of the near point of the depth of field.

When the upper limit of Condition (5) above is not satisfied, the depth of field becomes small and ensuring a desired resolution for the object distant A1 leads to an out-of-focus image for the object distant B1. On the other hand, when the lower limit of Condition (5) above is not satisfied, it is difficult to ensure a desired resolution for the object distance A1. Furthermore, when the upper limit of Condition (6) above is not satisfied, the optical diffraction limit is surpassed, and excellent images cannot be obtained even though the images are in-focus. On the other hand, when the lower limit of Condition (6) above is not satisfied, the depth of field becomes small and ensuring a desired resolution for the object distant A1 leads to an out-of-focus image for the object distant B1. For example, it is preferable for the capsule endoscope having an outer diameter of approximately 10 mm that the object distance A1 be 3 mm and the object distance B1 be 50 mm.

Also, in such cases, it is preferable to provide structures to control the orientation of the capsule so that the optical system for acquiring the front images is oriented in the capsule insertion direction when the capsule endoscope reaches the esophagus or other examination target.

Figure 23:
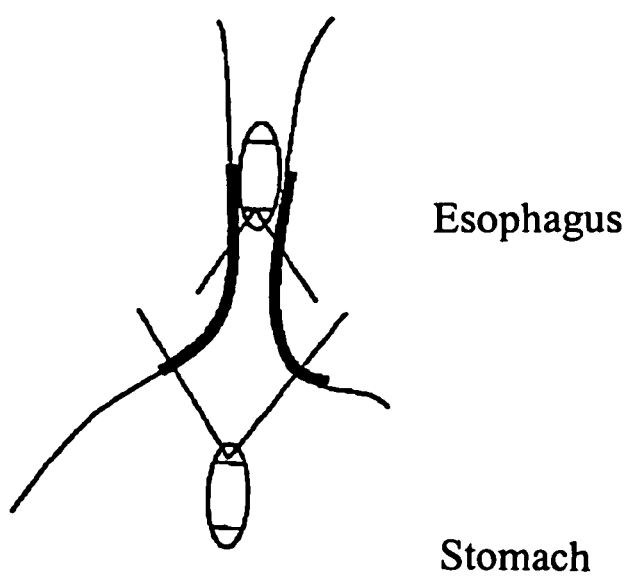
FIG. 23 is a schematic illustration of a capsule endoscope passing through the junction between the esophagus and the stomach.

In the capsule endoscope of the present invention, it is preferable that the illuminator for illuminating the front object and the illuminator for illuminating the back object emit light beams that are different from each other in brightness. For example, when the esophagus is observed from the stomach as shown in FIG. 23, unlike a small space within the esophagus being illuminated, a larger space is illuminated and the observation target site tends to be subject to insufficient illumination. It is preferable that the number of illuminators or the electric current through the illuminator be increased at the back of the capsule endoscope so that the back object is subject to brighter illumination.

It is further preferable that the illuminator emits a variable amount of light depending on the current position within the body. For example, when the capsule endoscope has reached the stomach, the illuminator for illuminating the back object is supplied with an electric current that is increased with a control device (not shown in the drawings). In this way, power consumption can be increased only when necessary and otherwise reduced, and the observation time within the digestive tract until the capsule endoscope is discharged can be extended.

One of the special image observation techniques used in combination with general color image observation to easily find lesions is called Narrow Band Imaging (hereinafter termed NBI) wherein a narrow band of light is emitted onto living tissue and reflected light from the living tissue is imaged. This technique has the following characteristics. An exemplary characteristic is that short wavelength light, such as blue light that does not penetrate deep inside living tissue, is used. Therefore, when a narrow band of short wavelength light is used in the NBI, the short wavelength light is reflected, carrying only the information on the living tissue surface and its surroundings. By detecting the reflected light, observation images specific for the living tissue surface can be obtained. On the other hand, when red light, which penetrates deep inside living tissue, is used in the NBI, when this long wavelength light is reflected, this long wavelength reflected light carries information of the deep parts of the living tissue. Thus, the deep parts of the living tissue can be imaged. Using NBI, mucoepidermoid capillary blood vessels, for example, can be clearly observed without dispersing dye on the living tissue surface or injecting an imaging agent such as Indocyanine green (ICG) around a tumor developing in the living tissue. In the capsule endoscope of the present invention, NBI can be used in combination with general color image observation in order to improve the accuracy of diagnosis of "Barrett's esophagus." It is preferable that, for example, a white LED and a blue LED be used as illuminators and that the blue LED be turned on only when the observation target site is in the vicinity of the near point of the depth of field of the objective optical system so that NBI images can be obtained.

FIGS. 7-20 that are discussed below relate primarily to imaging of a front object. However, similar considerations relate to optical structures that are similar to those described below but generally not illustrated in FIGS. 7-20 that relate to imaging a back object. FIG. 8(a) does show optical structures 2b and 5b that are similar to the optical structures 2a and 5a, respectively, but as with optical structures not illustrated in FIGS. 7-20, their operation is not discussed. However, other corresponding optical structures for imaging of a back object (not illustrated in the drawings) may be determined generally on the same considerations of symmetry of imaging front and back objects as is apparent with regard to the optical structures 2b and 5b and the optical structures 2a and 5a, and their operation may be understood as similar or the same as the operation of the corresponding illustrated optical structures.

Figure 7:
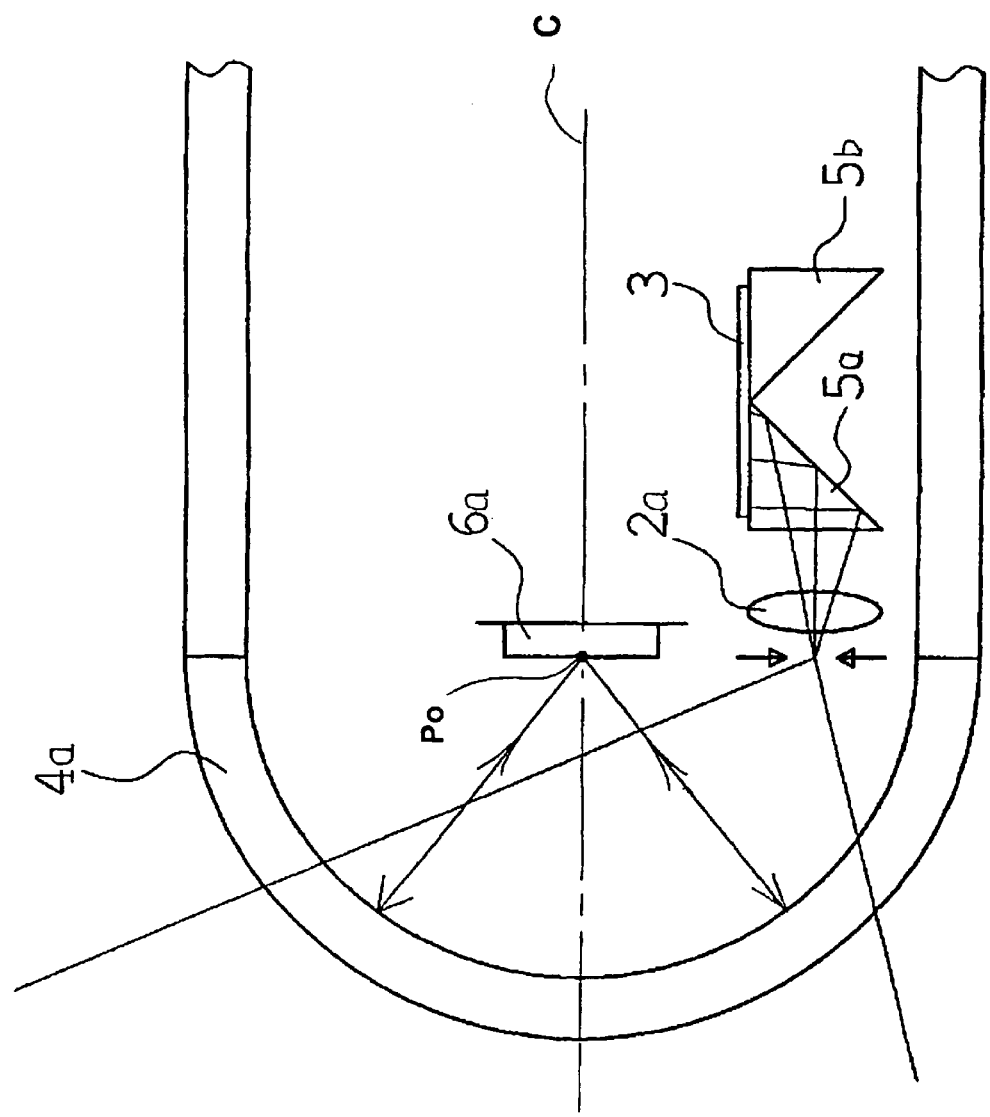
FIG. 7 illustrates the positional relationship between an illuminator and an objective optical system of the capsule endoscope of the present invention.
Figure 8A:
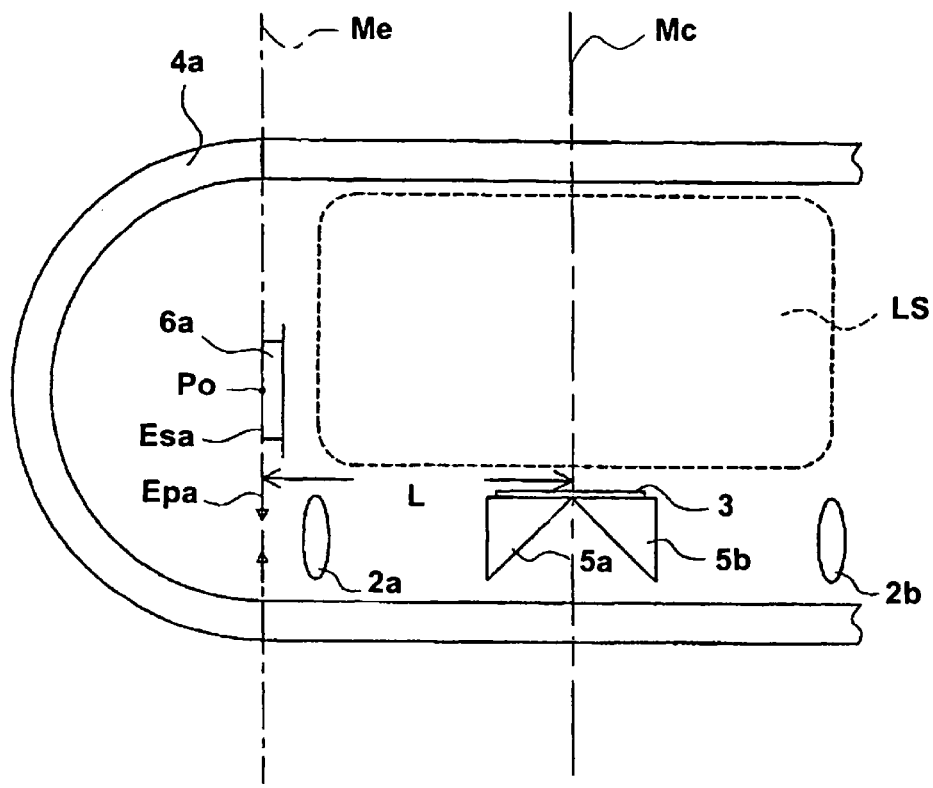
FIGS. 8(a) and 8(b) illustrate the positional relationship between the entrance pupil position of an objective optical system and the emission surface of an illuminator of the capsule endoscope of the present invention, with FIG. 8(a) illustrating a preferable positional relationship in the capsule endoscope of the present invention, and FIG. 8(b) illustrating an unfavorable positional relationship (in which the illuminator eclipses the field of view of the objective optical system) for comparison with FIG. 8(a)

FIG. 7 illustrates the positional relationship between an illuminator and an objective optical system of the capsule endoscope of the present invention. It is preferable in the capsule endoscope of the present invention that the illuminator 6a be placed at the spherical center Po of the dome-shaped transparent cover 4a as shown in FIG. 7. In the capsule endoscope of the present invention, the objective optical system 2a is placed off the central axis C of the capsule endoscope. In such a case, depending on the position of the illuminator 6a, some light emitted by the illuminator 6a and reflected by the inner surface of the dome-shaped transparent cover 4a may enter the objective optical system 2a and causes flare, impairing observation. Light is reflected to the image pickup device 3 by reflection from the reflecting surface of reflecting prism 5a, and similarly light from the back of the capsule endoscope related to optical structures (not shown in FIG. 7) similar to optical structures 2a, 4a, and 6a cause light to be reflected from the reflecting surface of reflecting prism 5b to the image pickup device 3.

As shown in FIG. 7, the illuminator 6a is placed at the spherical center Po of the dome-shaped transparent cover 4a so that light emitted by the illuminator 6a and reflected by the inner surface of the dome-shaped transparent cover 4a (4b) returns to the spherical center Po and never enters the objective optical system 2a.

Figure 8B:
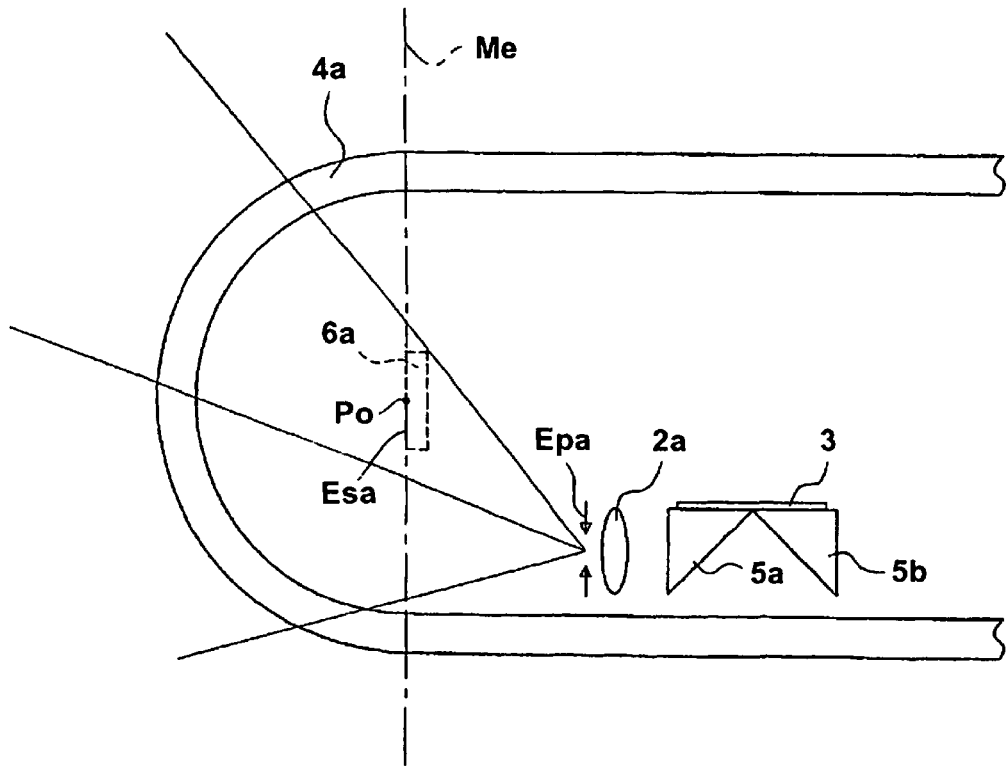

FIGS. 8(a) and 8(b) illustrate the positional relationship between the entrance pupil position of an objective optical system and the emission surface of an illuminator of the capsule endoscope of the present invention, with FIG. 8(a) illustrating a preferable positional relationship in the capsule endoscope of the present invention, and FIG. 8(b) illustrating an unfavorable positional relationship (in which the illuminator eclipses the field of view of the objective optical system) for comparison with FIG. 8(a).

With reference to FIG. 8(a), it is preferable in the capsule endoscope of the present invention that the entrance pupil EPa of the objective optical system 2a and the emission surface ESa of the illuminator 6a are on the same imaginary plane Me.

With reference to FIG. 8(b), when the entrance pupil EPa of the objective optical system 2a is behind the emission surface ESa of the illuminator 6a, the field of view of the objective optical system 2a may be blocked by the illuminator 6a. On the other hand, with reference to FIG. 8(a), when the entrance pupil EPa of the objective optical system 2a and the emission surface ESa of the illuminator 6a are on the same imaginary plane Me, the field of view of the objective optical system 2a is not blocked by the illuminator 6a.

In this case, it is preferable that the objective optical system 2a be constructed in a manner that the optical path length L between the entrance pupil EPa of the objective optical system 2a and the reflecting prism 5a, which is equal to the distance between the imaginary plane Me and the imaginary plane Mc, where Mc is an imaginary plane that passes through the center of the effective image pickup area of the image pickup device 3, is as large as possible, as illustrated in FIG. 8(a).

With this structure, a large space LS is created between the illuminator 6a and the corresponding illuminator (such as 6b, not shown in the drawings) for forming a back image in the direction opposite to the capsule insertion direction, and an electrical circuit for controlling the emissions of the illuminators can be provided immediately behind one of the illuminators while image processing, memory, and communication circuits (and even batteries) can be efficiently placed near the image pickup device 3.

It is further preferable in the capsule endoscope of the present invention that the objective optical system 2a be a retrofocus optical system. As shown in FIG. 1, in order to provide a reflecting prism 5a (5b) that folds the optical axis of the objective optical system 2a (2b) toward the image pickup surface of the image pickup device 3, the objective optical system 2a (2b) must have a large back focus. For example, using a retrofocus optical system formed of, from the object side, a lens group having negative refractive power and a lens group having positive refractive power, the objective optical system 2a (2b) can have a large back focus and the reflecting prism 5a (5b) can be easily placed. The entrance surface of the reflecting prism 5a (5b) can be a lens surface, which is preferable because aberrations caused by the objective optical system 2a (2b) can be easily corrected.

Embodiments 1-6 of the present invention will now be individually described with further reference to the drawings. The capsule endoscopes of these embodiments are designed as described above to similarly form images of both front and back objects. However, as with FIGS. 1-8(b) described above, the capsule endoscopes of Embodiments 1-6 will primarily be described with reference to the formation of images of front objects.

Embodiment 1

Figure 9:
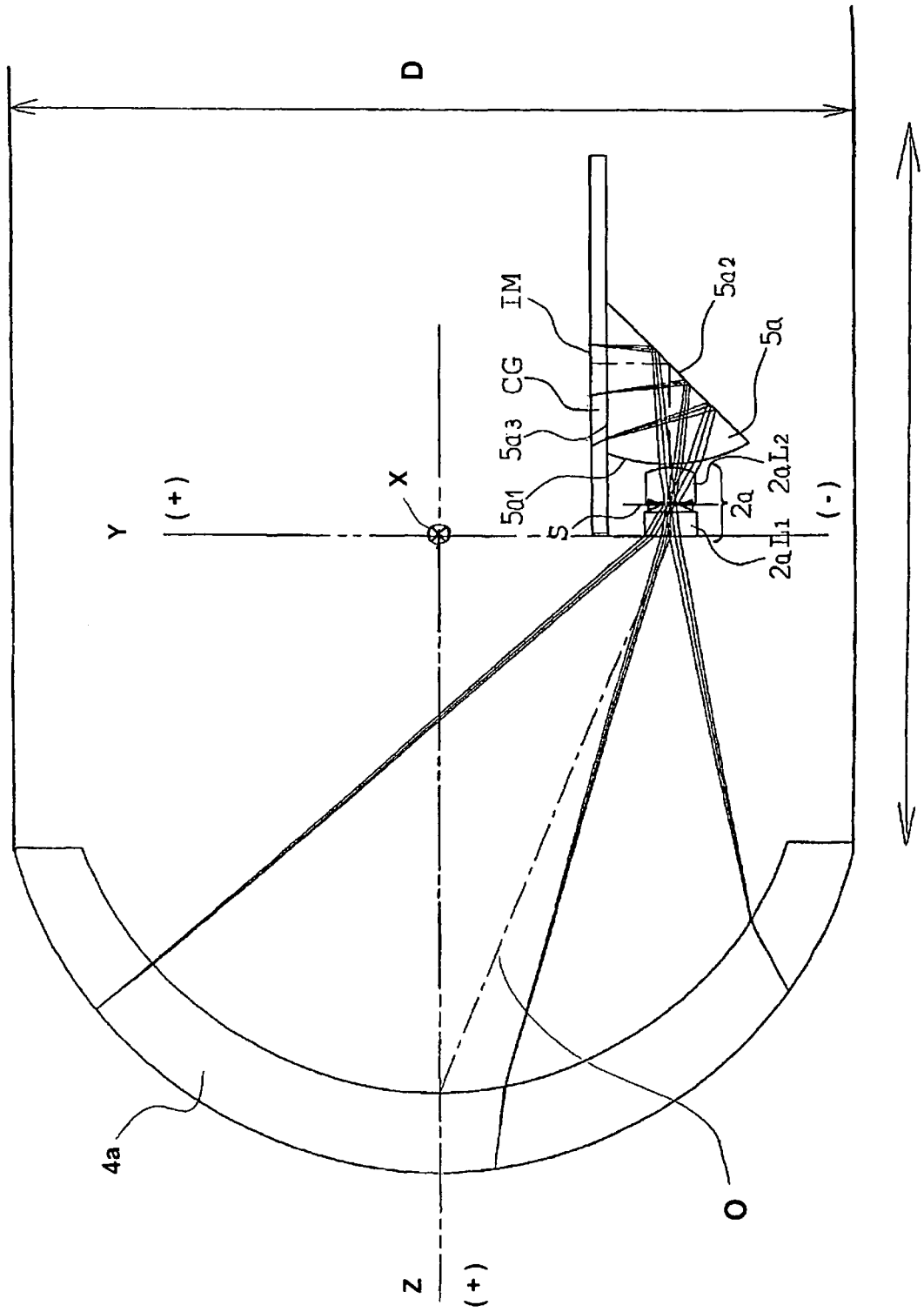
FIG. 9 is a cross-sectional view along the optical axis of the optical structure from the transparent cover to the image pickup device of the capsule endoscope of Embodiment 1.
Figure 10:
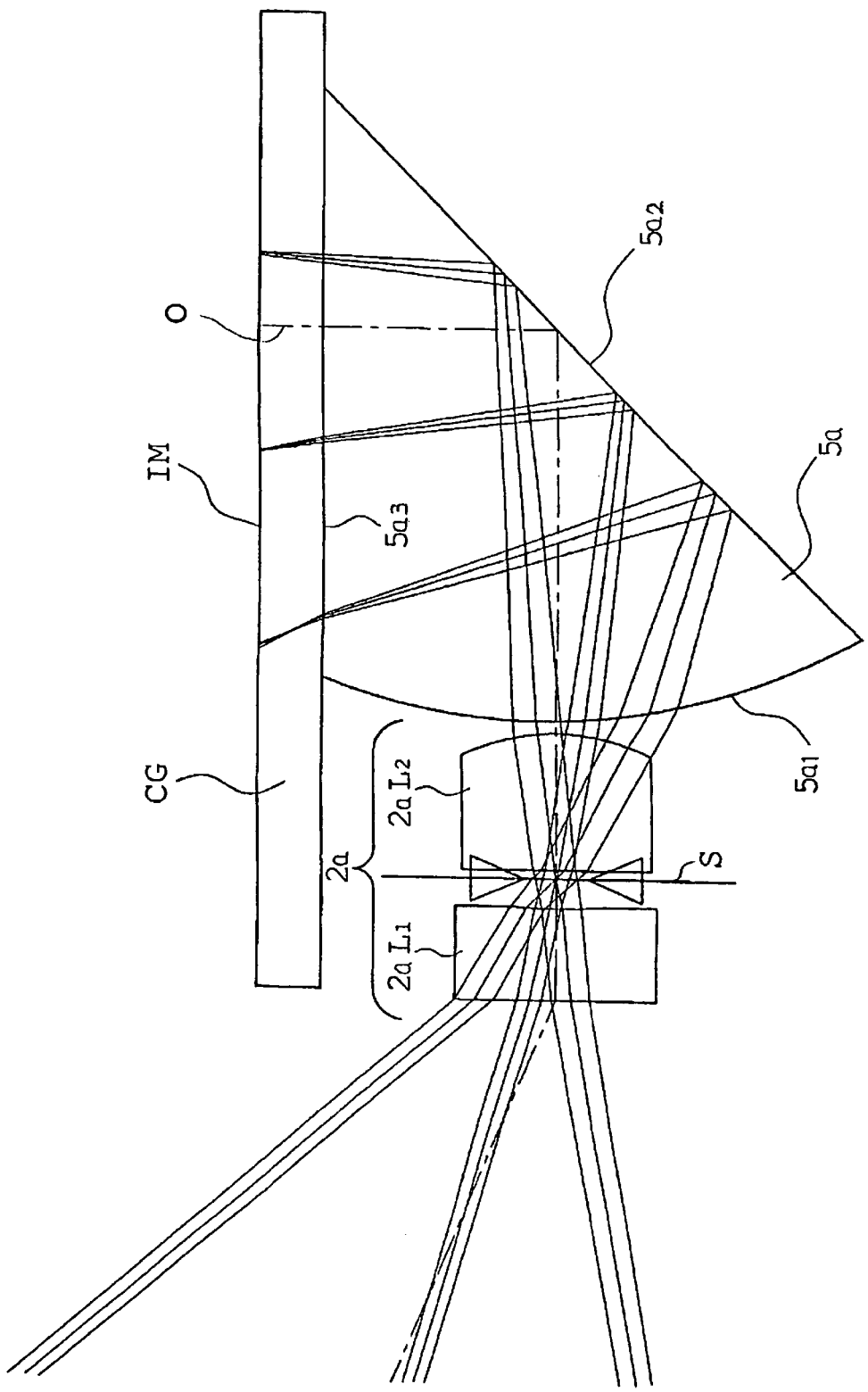
FIG. 10 is an enlarged view of an objective optical system and an image pickup device shown in FIG. 9.

FIG. 9 is a cross-sectional view along the optical axis of the optical structure from the transparent cover to the image pickup device of the capsule endoscope of Embodiment 1. FIG. 10 is an enlarged view of the objective optical system and image pickup device shown in FIG. 9. For convenience of illustration, only one optical system is illustrated.

In the capsule endoscope of Embodiment 1, the objective optical system 2a, the reflecting prism 5a, and the image pickup device 3 are arranged completely off the central axis of the dome-shaped transparent cover 4a, which coincides with the central axis of the capsule endoscope. In FIGS. 9 and 10, S is an aperture diaphragm, CG is a cover glass for protecting the image pickup surface of the image pickup device, and IM is the image pickup surface of the image pickup device. The capsule insertion direction and the opposite direction are indicated by a double-headed horizontal arrow at the bottom of FIG. 9. Additionally, the outer diameter of the capsule endoscope is indicated by the double-headed vertical arrow labeled D in FIG. 9. The optical axis O of the objective optical system is indicated by a single-dashed line, and the center axis of the capsule endoscope body is indicated by the double-dashed line.

The objective optical system 2a includes, from the object side, a plano-concave lens element 2aL1, a diaphragm S, and a plano-convex lens element 2aL2. The reflecting prism 5a arranged between the objective optical system 2a and the image pickup surface IM of the image pickup device has a first (entrance) surface 5a1 that is convex, a second reflecting surface 5a2 that is planar, and a third surface 5a3 that is planar. Light from the objective optical system 2a enters the reflecting prism 5a from the first surface, is reflected toward the image pickup surface IM of the image pickup device by the second surface, and exits from the third surface.

The image pickup device of the capsule endoscope of Embodiment 1 is placed with the image pickup surface IM facing the outside of the capsule endoscope rather than facing the central axis of the capsule endoscope.

Table 1 below lists the design data of the transparent cover, the objective optical system, and the reflecting prism of the capsule endoscope of Embodiment 1. More specifically, Table 1 lists the optical element surfaces in order from the object side, the radius of curvature r of each optical surface, the on-axis distance d between optical surfaces, as well as the refractive index Nd and the Abbe number vd (both measured at the d-line) of the optical material on the image side of the optical element surface.

When an optical element surface (call it surface # k) is eccentric to the optical element surface immediately next to it on the object side (hence surface # k−1), the following relationships apply. For example in FIG. 9, the object-side surface of the plano-concave lens element 2aL1 (surface #3 in Table 1 below) is eccentric to the image-side surface of the transparent cover 4a (surface #2 in Table 1). Table 2 below lists the shift (in x, y, and z coordinates in FIG. 9) of the vertex of surface #3 from the origin of coordinates (hereinafter 'origin') and the inclinations (angles α, β, γ) of surface #3 about the coordinate axes X, Y and Z respectively, with the origin being a point shifted from the vertex of surface #2 toward the image by the on-axis distance between the surfaces 2 and 3, which is seven millimeters. Herein, it is assumed that a line passing through the origin and coinciding with an outer diameter direction of the capsule endoscope is the Y-axis, the line passing through the origin and coinciding with the capsule insertion direction is the Z-axis, and the line passing through the origin and orthogonal to both the Y-axis and the Z-axis is the X-axis. For flat optical element surfaces, the vertex of an optical element surface is defined as the point of intersection of the optical element surface and the optical axis. In FIG. 9, values on the Y-axis are positive above the origin and negative below the origin; values on the Z-axis are positive to the left of the origin and negative to the right of the origin; and values on the X-axis are positive towards the viewer of the figure and negative away from the viewer of the figure. The inclination angle of an optical element surface about the X-axis as the axis of rotation is the angle α; the inclination angle of an optical element surface about the Y-axis as the axis of rotation is the angle β; and the inclination angle of an optical element surface about the Z-axis as the axis of rotation is the angle γ. The sign of an inclination is positive for the counterclockwise direction. According to Table 2, the vertex of surface #3 is shifted from the origin by −3 mm in the Y-axis direction.

Similarly, in FIG. 9, the reflecting surface of the reflecting prism 5a (surface #9 in Table 1) is eccentric to the entrance surface of the reflecting prism 5a (surface #8 in Table 1). Table 2 lists the shifts (x, y, z) of the vertex of surface #9 from the origin and the inclinations (α, β, γ) of surface #9 about the coordinate axes as the axes of rotation, with the origin being a point shifted from the vertex of surface #8 toward the image by the on-axis distance between surfaces 8 and 9, which is 1.3 mm. According to Table 2, surface #9 is tilted forty-five degrees about the X-axis as the axis of rotation.

As described above, when surface k is eccentric, the eccentricity of surface k is indicated by defining a point shifted from the vertex of surface k−1 toward the image by the on-axis distance between surfaces k−1 and k.

In all of Embodiments 1-6 described below, the design data and eccentric data are

TABLE 1

| Surface # | radius of curvature r | surface distance d | refractive index Nd | Abbe No. vd |
|---|---|---|---|---|
| 1 | 5.5000 | 1.0000 | 1.51825 | 64.14 |
| 2 | 4.8000 | 7.0000 | 1.0 | |
| 3 | ∞ | 0.3000 | 1.51825 | 64.14 |
| 4 | 1.5000 | 0.1000 | 1.0 | |
| 5 | ∞ (aperture diaphragm) | 0.0300 | 1.0 | |
| 6 | ∞ | 0.4500 | 1.51825 | 64.14 |
| 7 | −0.700 | 0.0300 | 1.0 | |
| 8 | 2.0000 | 1.3000 | 1.51825 | 64.14 |
| 9 | ∞ | 1.0000 | 1.51825 | 64.14 |
| 10 | ∞ | 0.2000 | 1.51825 | 64.14 |
| 11 | ∞ | 0.0 | 1.0 | |

TABLE 1-continued

| Surface # | radius of curvature r | surface distance d | refractive index Nd | Abbe No. vd |
|---|---|---|---|---|
| 12 | ∞ (image pickup surface) | | | |

TABLE 2

| Surface #. | x (mm) | y (mm) | z (mm) | α (°) | β (°) | γ (°) |
|---|---|---|---|---|---|---|
| 3 | 0.0 | −3.0 | 0.0 | 0.0 | 0.0 | 0.0 |
| 9 | 0.0 | 0.0 | 0.0 | 45.0 | 0.0 | 0.0 |

Embodiment 2

Figure 11:
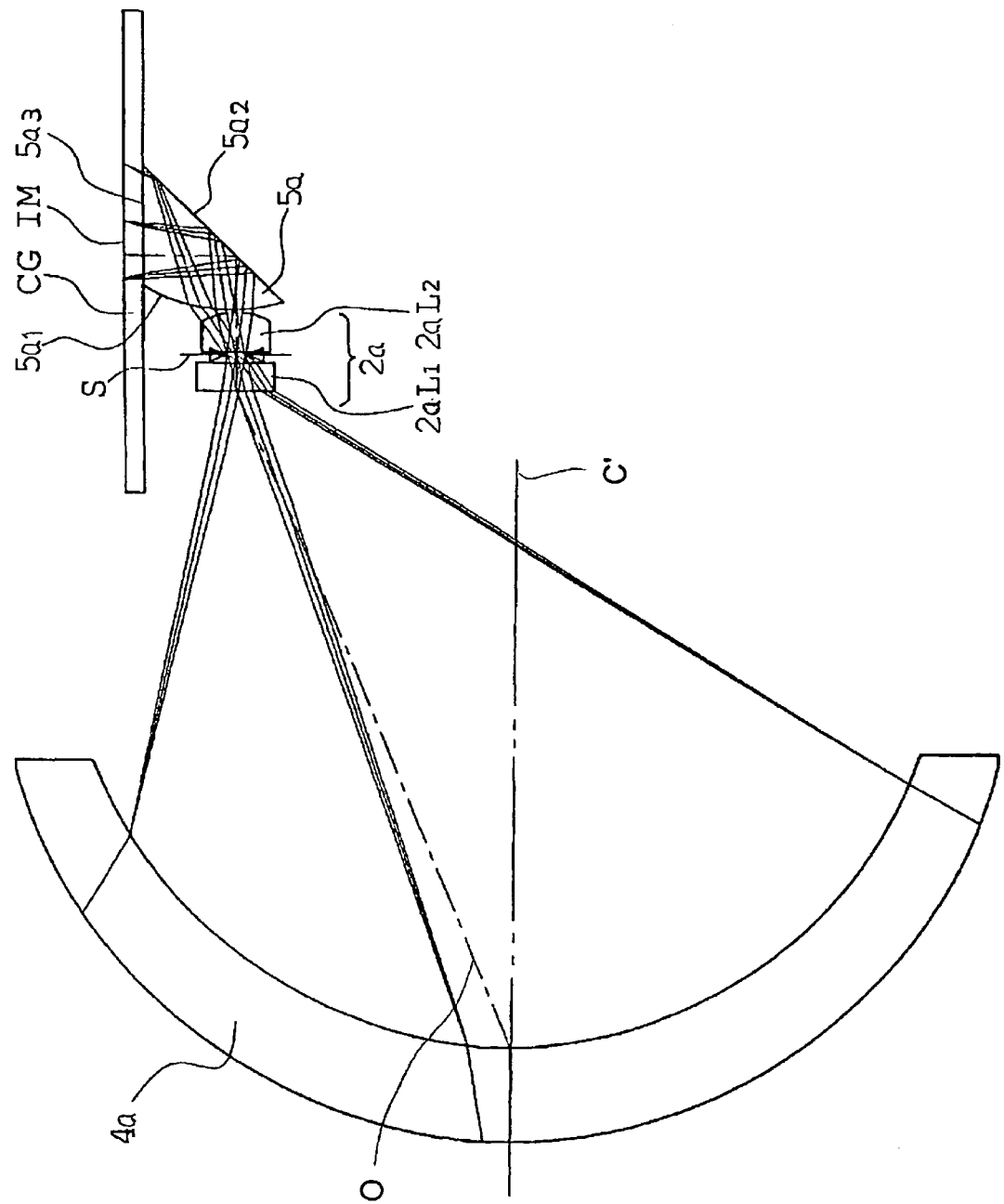
FIG. 11 is a cross-sectional view along the optical axis of the optical structure from the transparent cover to the image pickup device of the capsule endoscope of Embodiment 2.
Figure 12:
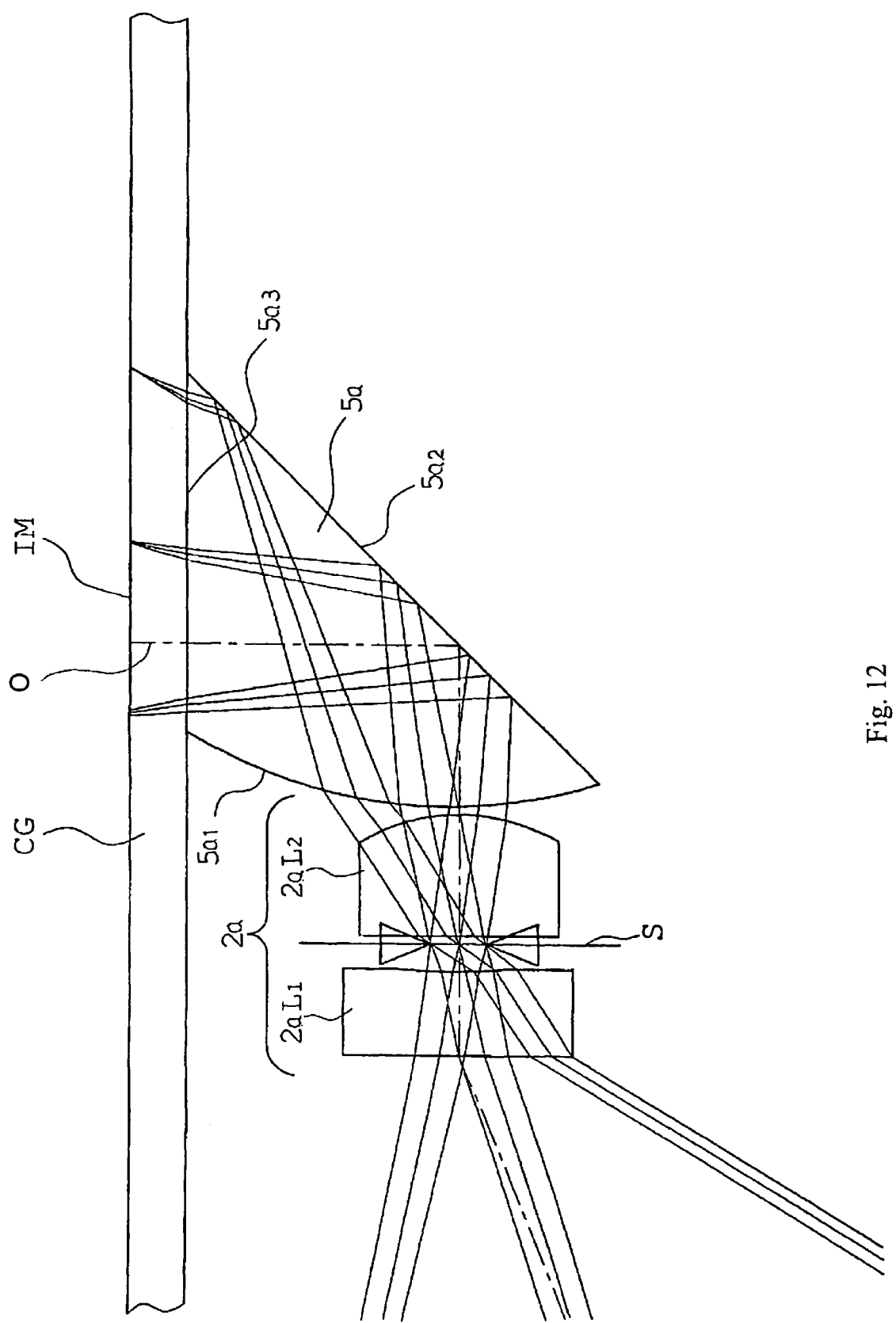
FIG. 12 is an enlarged view of the objective optical system and the image pickup device shown in FIG. 11.

FIG. 11 is a cross-sectional view along the optical axis of the optical structure from the transparent cover to the image pickup device of the capsule endoscope of Embodiment 2. FIG. 12 is an enlarged view of the objective optical system and image pickup device shown in FIG. 11. For convenience of illustration, only one objective optical system is illustrated. The optical axis O of the objective optical system is indicated by a single-dashed line in FIGS. 11 and 12 and the central axis of the transparent cover is denoted as C' in FIG. 11.

In the capsule endoscope of Embodiment 2, the objective optical system 2a, the reflecting prism 5a, and the image pickup device are arranged completely off the central axis of the dome-shaped transparent cover 4a, which coincides with the central axis of the capsule endoscope. In FIGS. 11 and 12, S is an aperture diaphragm, CG is a cover glass for protecting the image pickup surface of the image pickup device, and IM is the image pickup surface of the image pickup device.

The objective optical system 2a includes, from the object side, a plano-concave lens element 2aL1, an aperture diaphragm S, and a plano-convex lens element 2aL2. The reflecting prism 5a arranged between the objective optical system 2a and the image pickup surface IM of the image pickup device has a first (entrance) surface 5a1 that is convex, a second reflecting surface 5a2 that is planar, and a third reflecting surface 5a3 that is planar. Light from the objective optical system 2a enters the reflecting prism from the first surface, is reflected toward the image pickup surface IM of the image pickup device by the second surface, and exits from the third surface.

The image pickup device of the capsule endoscope of Embodiment 2 is placed with the image pickup surface IM facing the central axis of the capsule endoscope.

Tables 3 and 4 below list the design data and eccentric data of the transparent cover, the objective optical system, and the reflecting prism of the capsule endoscope of Embodiment 2.

TABLE 3

| Surface # | radius of curvature r | surface distance d | refractive index Nd | Abbe No. vd |
|---|---|---|---|---|
| 1 | 5.5000 | 1.0000 | 1.51825 | 64.14 |
| 2 | 4.8000 | 7.0000 | 1.0 | |
| 3 | ∞ | 0.3000 | 1.51825 | 64.14 |
| 4 | 3.0000 | 0.1000 | 1.0 | |
| 5 | ∞ (aperture diaphragm) | 0.0300 | 1.0 | |
| 6 | ∞ | 0.4500 | 1.51825 | 64.14 |
| 7 | −0.700 | 0.0300 | 1.0 | |
| 8 | 2.0000 | 0.6000 | 1.51825 | 64.14 |
| 9 | ∞ | 1.2000 | 1.51825 | 64.14 |

TABLE 3-continued

| Surface # | radius of curvature r | surface distance d | refractive index Nd | Abbe No. vd |
|---|---|---|---|---|
| 10 | ∞ | 0.2000 | 1.51825 | 64.14 |
| 11 | ∞ | 0.0 | 1.0 | |
| 12 | ∞ (image pickup surface) | | | |

TABLE 4

| Surface #. | x (mm) | y (mm) | z (mm) | α (°) | β (°) | γ (°) |
|---|---|---|---|---|---|---|
| 3 | 0.0 | 3.0 | 0.0 | 0.0 | 0.0 | 0.0 |
| 9 | 0.0 | 0.0 | 0.0 | 45.0 | 0.0 | 0.0 |

Embodiment 3

Figure 13:
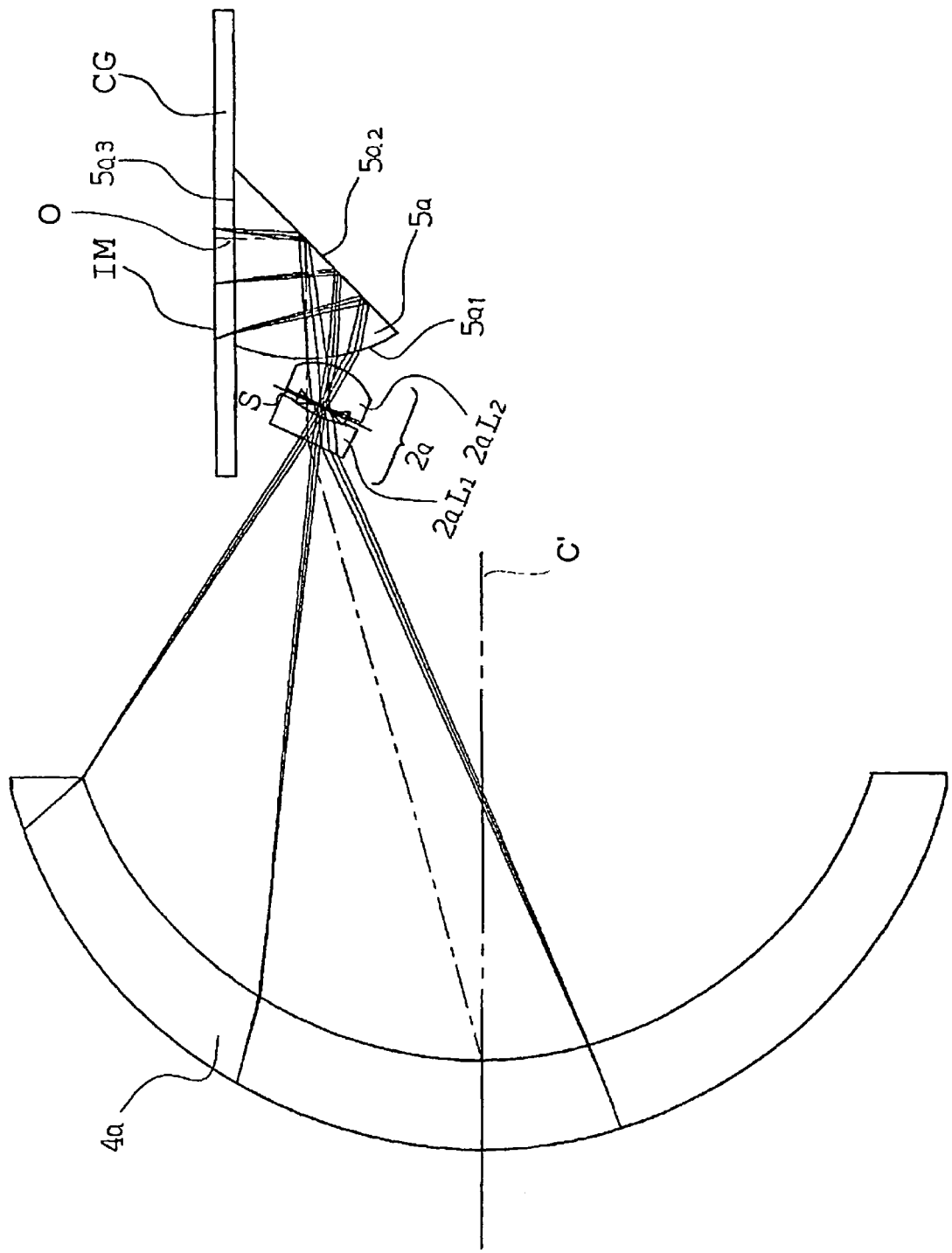
FIG. 13 is a cross-sectional view along the optical axis of the optical structure from the transparent cover to the image pickup device of the capsule endoscope of Embodiment 3.
Figure 14:
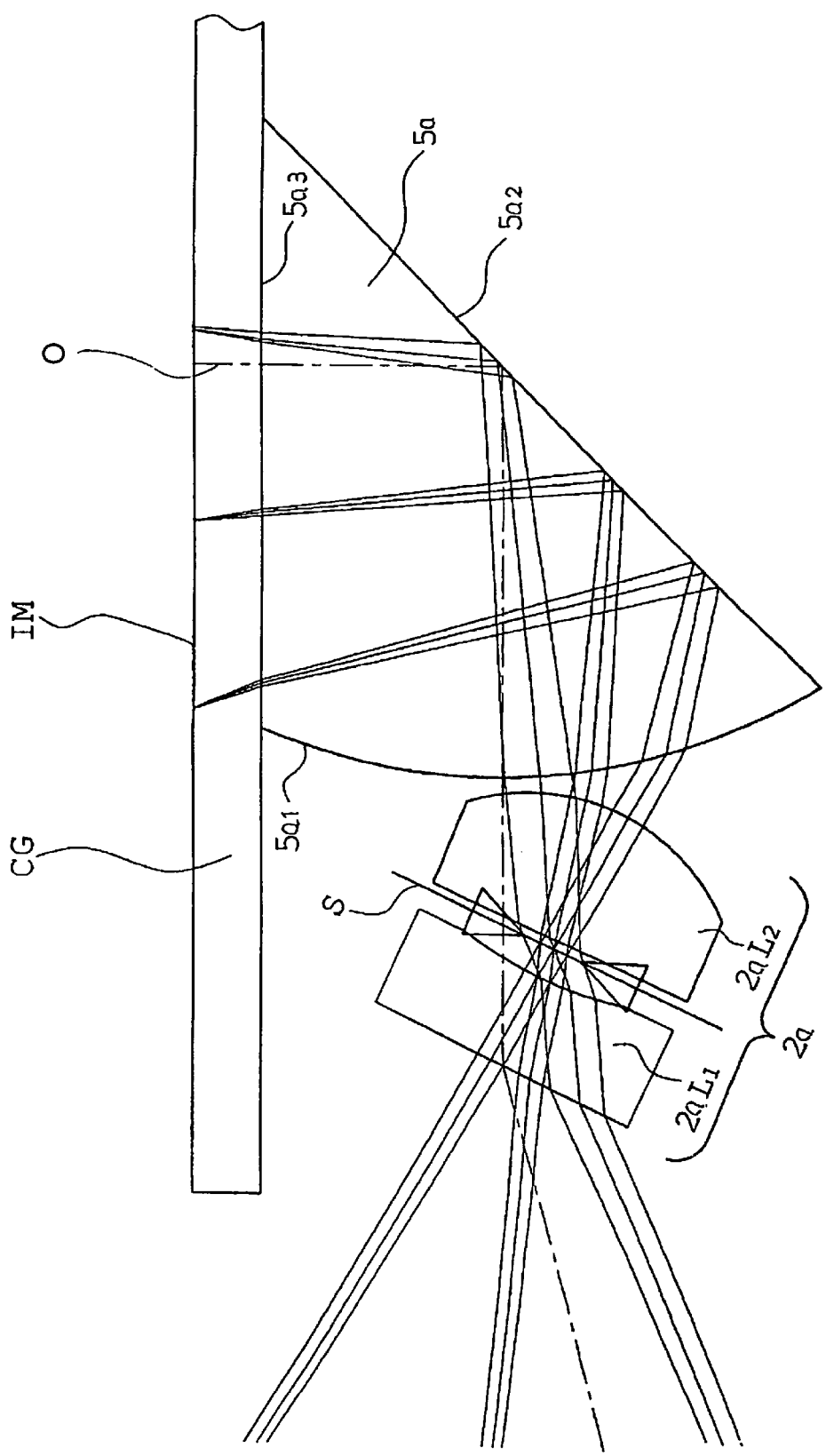
FIG. 14 is an enlarged view of an objective optical system and an image pickup device shown in FIG. 13.

FIG. 13 is a cross-sectional view along the optical axis of the optical structure from the transparent cover to the image pickup device of the capsule endoscope of Embodiment 3. FIG. 14 is an enlarged view of the objective optical system and image pickup device shown in FIG. 13. For convenience of illustration, only one objective optical system is illustrated. The optical axis O of the objective optical system is indicated by a single-dashed line in FIGS. 13 and 14 and the central axis of the transparent cover is denoted as C' in FIG. 13.

In the capsule endoscope of Embodiment 3, the objective optical system 2a, the reflecting prism 5a, and the image pickup device are arranged completely off the central axis of the dome-shaped transparent cover 4a, which coincides with the central axis of the capsule endoscope. In FIGS. 13 and 14, S is an aperture diaphragm, CG is a cover glass for protecting the image pickup surface of the image pickup device, and IM is the image pickup surface of the image pickup device.

The objective optical system 2a includes, from the object side, a plano-concave lens element 2aL1, an aperture diaphragm S, and a plano-convex lens element 2aL2. The objective optical system 2a is eccentric to the central axis of the capsule endoscope as a whole. The reflecting prism 5a provided between the objective optical system 2a and the image pickup surface IM of the image pickup device has a first (entrance) surface 5a1 that is convex, a second reflecting surface 5a2 that is planar, and a third reflecting surface 5a3 that is planar. Light from the objective optical system 2a enters the reflecting prism 5a from the first surface, is reflected toward the image pickup surface IM of the image pickup device by the second surface, and exits from the third surface.

The image pickup device of the capsule endoscope of this embodiment is placed with the image pickup surface IM facing the central axis of the capsule endoscope.

Tables 5 and 6 below list the design data and eccentric data of the transparent cover, the objective optical system, and the reflecting prism of the capsule endoscope of Embodiment 3.

TABLE 5

| Surface # | radius of curvature r | surface distance d | refractive index Nd | Abbe No. vd |
|---|---|---|---|---|
| 1 | 5.5000 | 1.0000 | 1.51825 | 64.14 |
| 2 | 4.8000 | 7.0000 | 1.0 | |
| 3 | ∞ | 0.3000 | 1.51825 | 64.14 |
| 4 | 1.5000 | 0.1000 | 1.0 | |
| 5 | ∞ (aperture diaphragm) | 0.0300 | 1.0 | |
| 6 | ∞ | 0.4500 | 1.51825 | 64.14 |
| 7 | −0.700 | 0.0300 | 1.0 | |
| 8 | 2.0000 | 1.3000 | 1.51825 | 64.14 |
| 9 | ∞ | 1.0000 | 1.51825 | 64.14 |
| 10 | ∞ | 0.2000 | 1.51825 | 64.14 |
| 11 | ∞ | 0.0 | 1.0 | |
| 12 | ∞ (image pickup surface) | | | |

TABLE 6

| Surface # | x (mm) | y (mm) | z (mm) | α (°) | β (°) | γ (°) |
|---|---|---|---|---|---|---|
| 3 | 0.0 | 2.0 | 0.0 | 65.0 | 0.0 | 0.0 |
| 9 | 0.0 | 0.0 | 0.0 | 45.0 | 0.0 | 0.0 |

In Embodiment 3, the objective optical system 2a is eccentric to the central axis of the capsule endoscope as a whole. Therefore, Table 6 only shows the shift (x, y, z) of the vertex of the object-most side surface of the objective optical system 2a (surface #3 in Table 6) and the inclination (α, β, γ) of surface #3 about the axes of coordinates as the axes of rotation.

Embodiment 4

Figure 15:
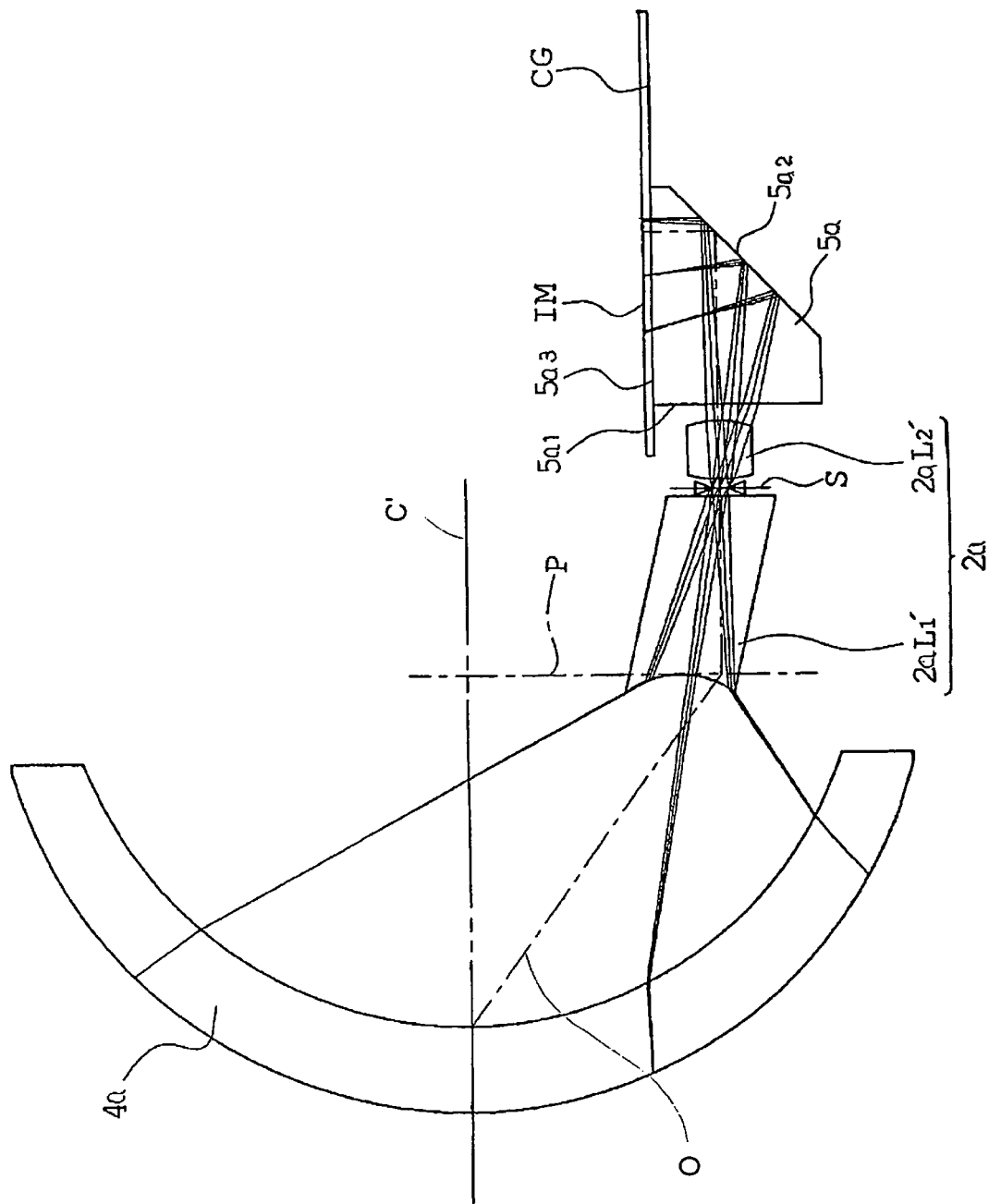
FIG. 15 is a cross-sectional view along the optical axis of the optical structure from the transparent cover to the image pickup device of the capsule endoscope of Embodiment 4.
Figure 16:
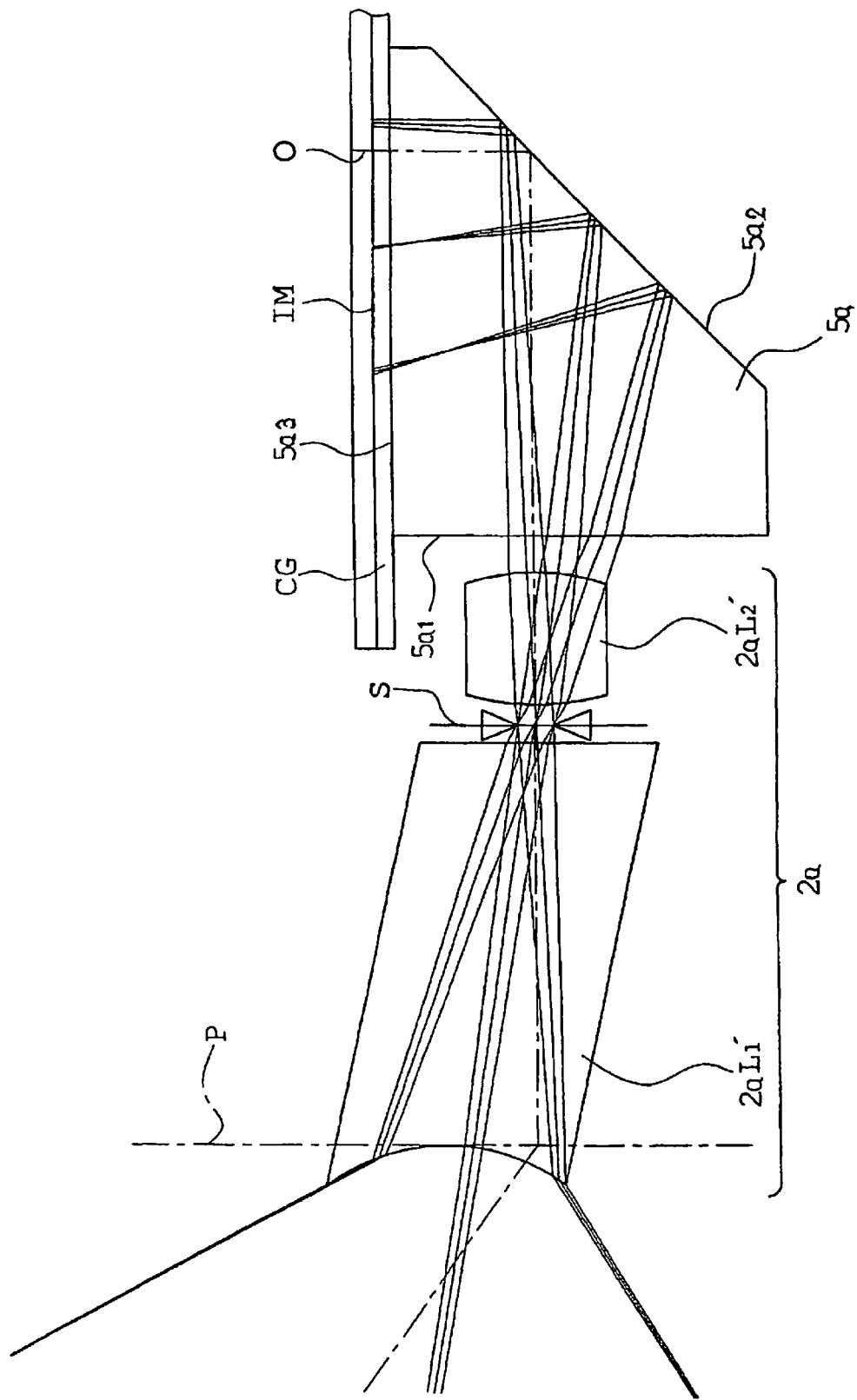
FIG. 16 is an enlarged view of an objective optical system and an image pickup device shown in FIG. 15.

FIG. 15 is a cross-sectional view along the optical axis of the optical structure from the transparent cover to the image pickup device of the capsule endoscope of Embodiment 4. FIG. 16 is an enlarged view of an objective optical system and image pickup device shown in FIG. 15. For convenience of illustration, only one objective optical system is illustrated. The optical axis O of the objective optical system is indicated by a single-dashed line in FIGS. 15 and 16 and the central axis of the transparent cover is denoted as C' in FIG. 15.

In the capsule endoscope of Embodiment 4, the objective optical system 2a, the reflecting prism 5a, and the image pickup device are provided completely off the central axis of the dome-shaped transparent cover 4a, which coincides with the central axis of the capsule endoscope. In FIGS. 15 and 16, S is an aperture diaphragm, CG is a cover glass for protecting the image pickup surface of the image pickup device, and IM is the image pickup surface of the image pickup device.

The objective optical system 2a includes, from the object side, a lens element 2aL1' that is concave on the object side and planar on the image side, an aperture diaphragm S, and a lens element 2aL2' that is convex on both sides.

The objective optical system 2a is arranged so that the entrance pupil is on an imaginary plane P that coincides with the emission surface of an illuminator (not illustrated in FIGS. 15 and 16). The reflecting prism 5a arranged between the objective optical system 2a and the image pickup surface IM of the image pickup device has a first (entrance) surface 5a1 that is planar, a second reflecting surface 5a2 that is planar, and a third reflecting surface 5a3 that is planar. Light from the objective optical system 2a enters the reflecting prism 5a from the first surface, is reflected toward the image pickup surface IM of the image pickup device by the second surface, and exits from the third surface.

The image pickup device of the capsule endoscope of Embodiment 4 is placed with the image pickup surface IM facing the outside of the capsule endoscope rather than facing the central axis.

Tables 7 and 8 list the design data and eccentric data of the transparent cover, the objective optical system, and the reflecting prism of the capsule endoscope of Embodiment 4.

TABLE 7

| Surface # | radius of curvature r | surface distance d | refractive index Nd | Abbe No. vd |
|---|---|---|---|---|
| 1 | 5.5000 | 1.0000 | 1.51825 | 64.14 |
| 2 | 4.8000 | 4.0000 | 1.0 | |
| 3 | −1.1000 | 2.1000 | 1.51825 | 64.14 |
| 4 | ∞ | 0.1000 | 1.0 | |
| 5 | ∞ (aperture diaphragm) | 0.1000 | 1.0 | |
| 6 | 1.3000 | 0.7000 | 1.51825 | 64.14 |
| 7 | −1.3000 | 0.2000 | 1.0 | |
| 8 | ∞ | 2.0000 | 1.51825 | 64.14 |
| 9 | ∞ | 1.0000 | 1.51825 | 64.14 |
| 10 | ∞ | 0.2000 | 1.51825 | 64.14 |
| 11 | ∞ | 0.0 | 1.0 | |
| 12 | ∞ (image pickup surface) | | | |

TABLE 8

| Surface # | x (mm) | y (mm) | z (mm) | α (°) | β (°) | γ (°) |
|---|---|---|---|---|---|---|
| 3 | 0.0 | −3.0 | 0.0 | 0.0 | 0.0 | 0.0 |
| 4 | 0.0 | −0.5 | 0.0 | 0.0 | 0.0 | 0.0 |
| 9 | 0.0 | 0.0 | 0.0 | 45.0 | 0.0 | 0.0 |

According to Table 8, the object-most side lens element 2aL1' of the objective optical system 2a is arranged so that the vertex of the image-side surface (surface #4 in Table 8) is shifted from the vertex of the object-side surface (surface #3 in Table 8) by −0.5 mm in the Y-axis direction.

Embodiment 5

Figure 17:
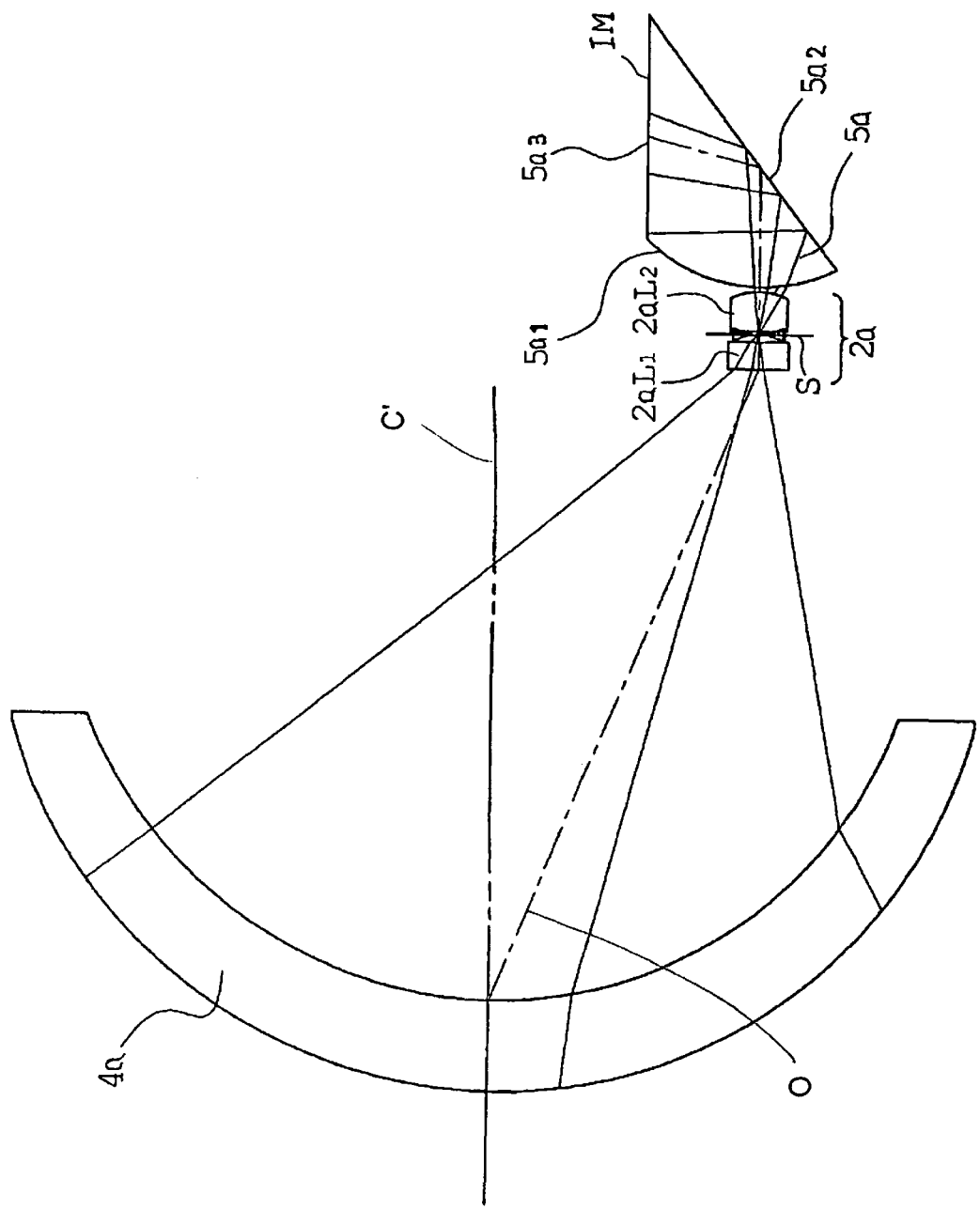
FIG. 17 is a cross-sectional view along the optical axis of the optical structure from the transparent cover to the image pickup device of the capsule endoscope of Embodiment 5.
Figure 18:
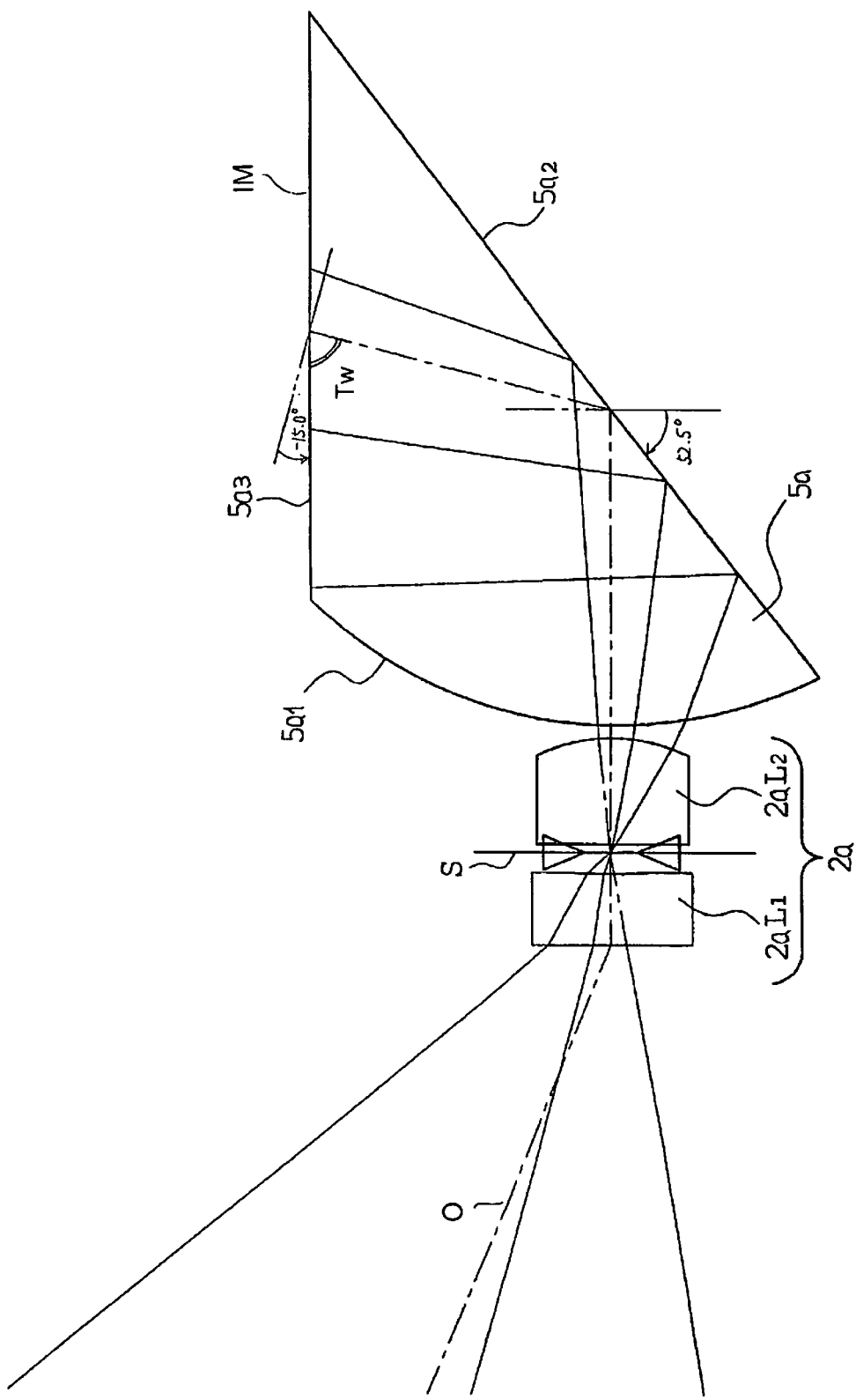
FIG. 18 is an enlarged view of an objective optical system and an image pickup device shown in FIG. 17.

FIG. 17 is a cross-sectional view along the optical axis of the optical structure from the transparent cover to the image pickup device of the capsule endoscope of Embodiment 5. FIG. 18 is an enlarged view of an objective optical system and image pickup device shown in FIG. 17. For convenience of illustration, only one objective optical system is illustrated. The optical axis O of the objective optical system is indicated by a single-dashed line in FIGS. 17 and 18 and the central axis of the transparent cover is denoted as C' in FIG. 17.

In the capsule endoscope of Embodiment 5, the objective optical system 2a, the reflecting prism 5a, and the image pickup device are provided completely off the central axis of the dome-shaped transparent cover 4a, which coincides with the central axis of the capsule endoscope. In FIGS. 17 and 18, S is an aperture diaphragm, and IM is the image pickup surface of the image pickup device.

The objective optical system 2a includes, from the object side, a plano-concave lens element 2aL1, an aperture diaphragm S, and a plano-convex lens element 2aL2. The reflecting prism 5a arranged between the objective optical system 2a and the image pickup surface IM of the image pickup device has a first (entrance) surface 5a1 that is convex, a second reflecting surface 5a2 that is planar, and a third surface 5a3 that is planar. The reflecting prism 5a is arranged so that the optical axis of the objective optical system 2a and the image pickup surface of the image pickup device form an angle Tw of seventy-five degrees. Light from the objective optical system 2a enters the reflecting prism 5a from the first surface, is reflected toward the image pickup surface IM of the image pickup device by the second surface, and exits from the third surface. The third surface 5a3 of the reflecting prism 5a is directly attached to the image pickup surface IM of the image pickup device without a cover glass for protecting the image pickup surface IM.

The image pickup device of the capsule endoscope of Embodiment 5 is placed with the image pickup surface IM facing the outside of the capsule endoscope rather than facing the central axis of the capsule endoscope.

Tables 9 and 10 below list the design data and eccentric data of the transparent cover, the objective optical system, and the reflecting prism of the capsule endoscope of Embodiment 5.

TABLE 9

| Surface # | radius of curvature r | surface distance d | refractive index Nd | Abbe No. vd |
|---|---|---|---|---|
| 1 | 5.5000 | 1.0000 | 1.51825 | 64.14 |
| 2 | 4.8000 | 7.0000 | 1.0 | |
| 3 | ∞ | 0.3000 | 1.51825 | 64.14 |
| 4 | 1.5000 | 0.1000 | 1.0 | |
| 5 | ∞ (aperture diaphragm) | 0.0300 | 1.0 | |
| 6 | ∞ | 0.4500 | 1.51825 | 64.14 |
| 7 | −0.700 | 0.0300 | 1.0 | |
| 8 | 2.0000 | 1.3000 | 1.51825 | 64.14 |
| 9 | ∞ | 1.3200 | 1.51825 | 64.14 |
| 10 | ∞ | 0 | 1.51825 | 64.14 |
| 11 | ∞(image pickup surface) | | | |

TABLE 10

| Surface # | x (mm) | y (mm) | z (mm) | α (°) | β (°) | γ (°) |
|---|---|---|---|---|---|---|
| 3 | 0.0 | −3.0 | 0.0 | 0.0 | 0.0 | 0.0 |
| 9 | 0.0 | 0.0 | 0.0 | 52.5 | 0.0 | 0.0 |
| 10 | 0.0 | 0.0 | 0.0 | −15.0 | 0.0 | 0.0 |

Embodiment 6

Figure 19:
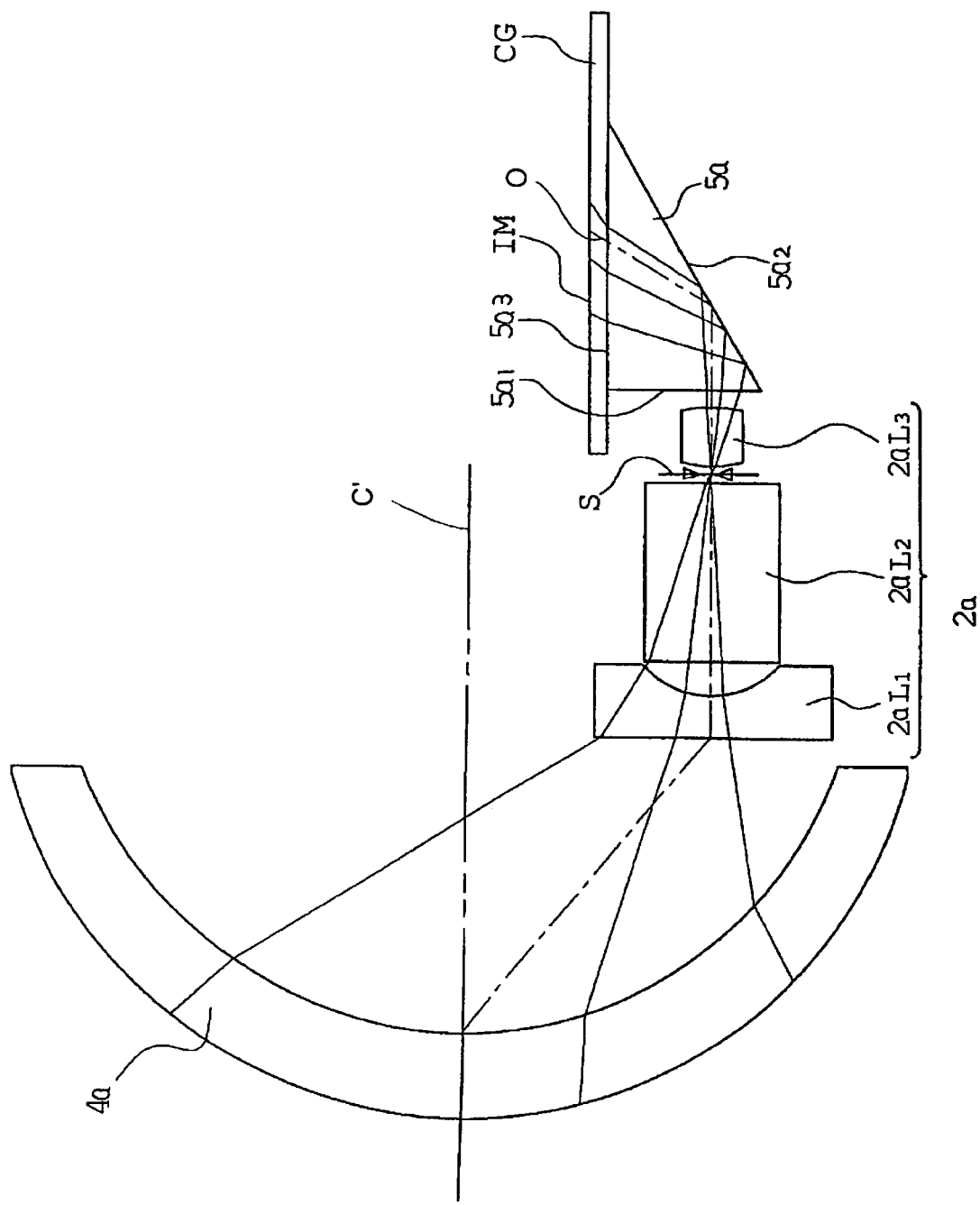
FIG. 19 is a cross-sectional view along the optical axis of the optical structure from the transparent cover to the image pickup device of the capsule endoscope of Embodiment 6.
Figure 20:
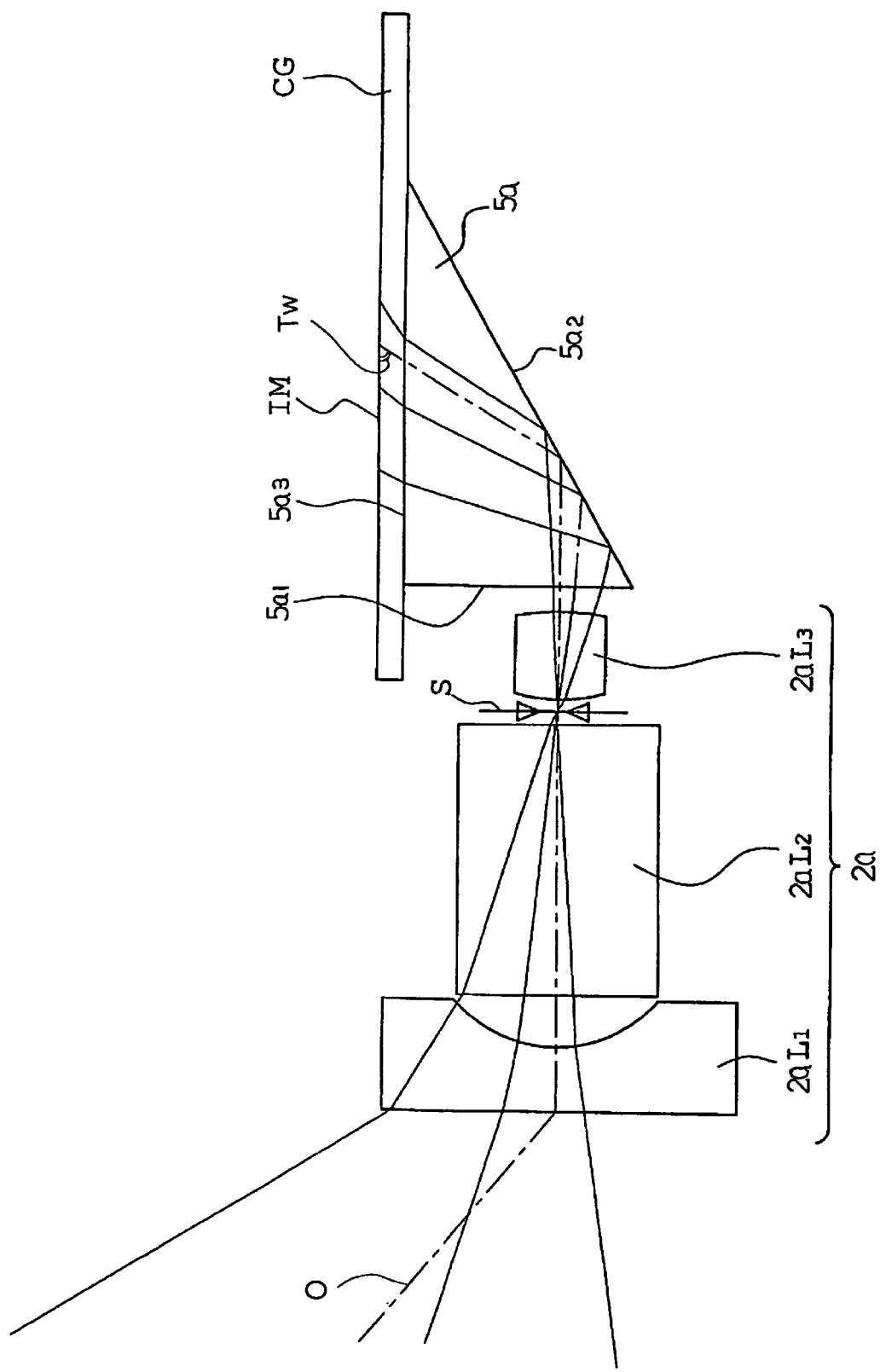
FIG. 20 is an enlarged view of an objective optical system and an image pickup device shown in FIG. 19.
Figure 21:
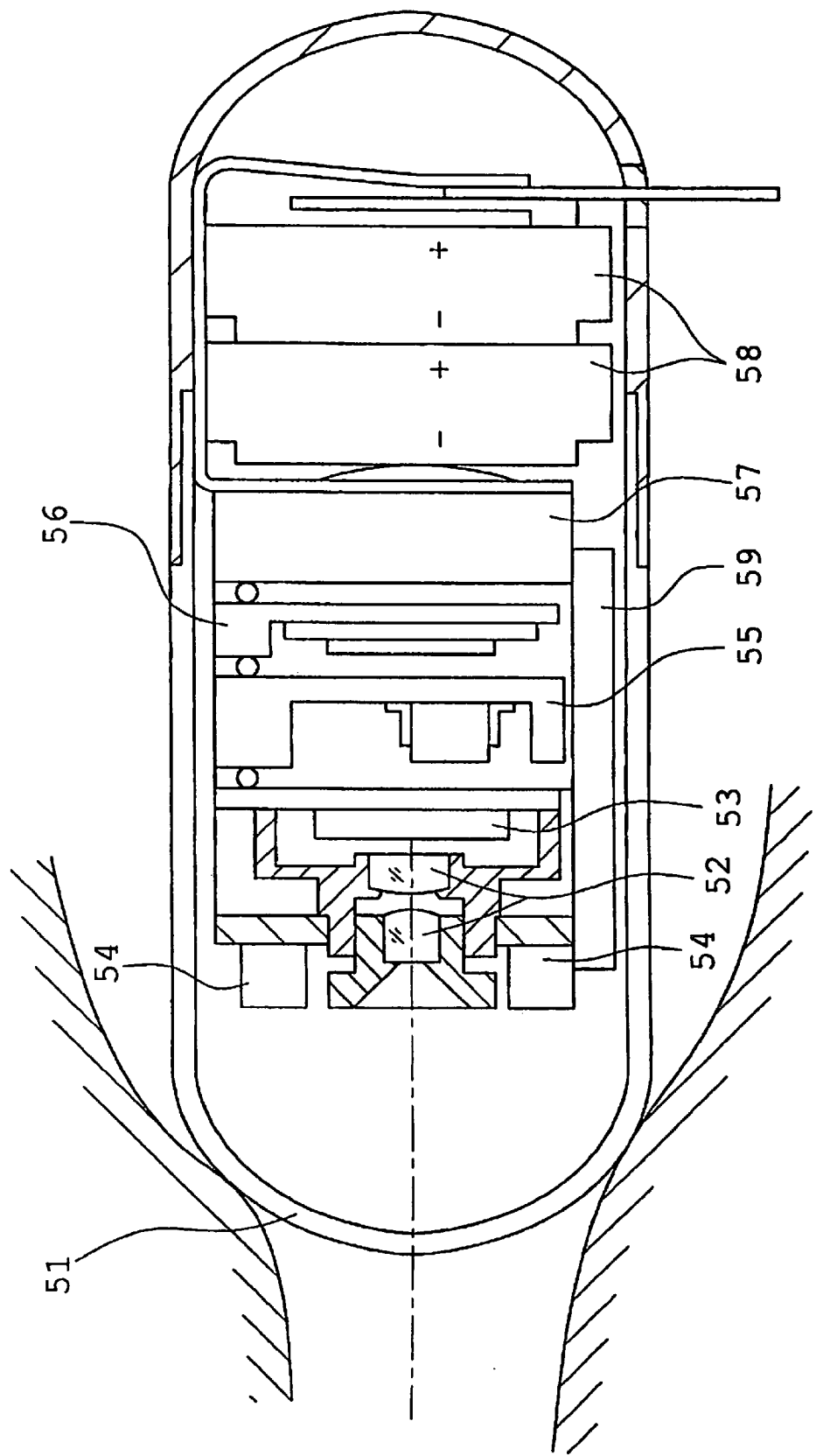
FIG. 21 illustrates the structure of a prior art capsule endoscope.
Figure 22:
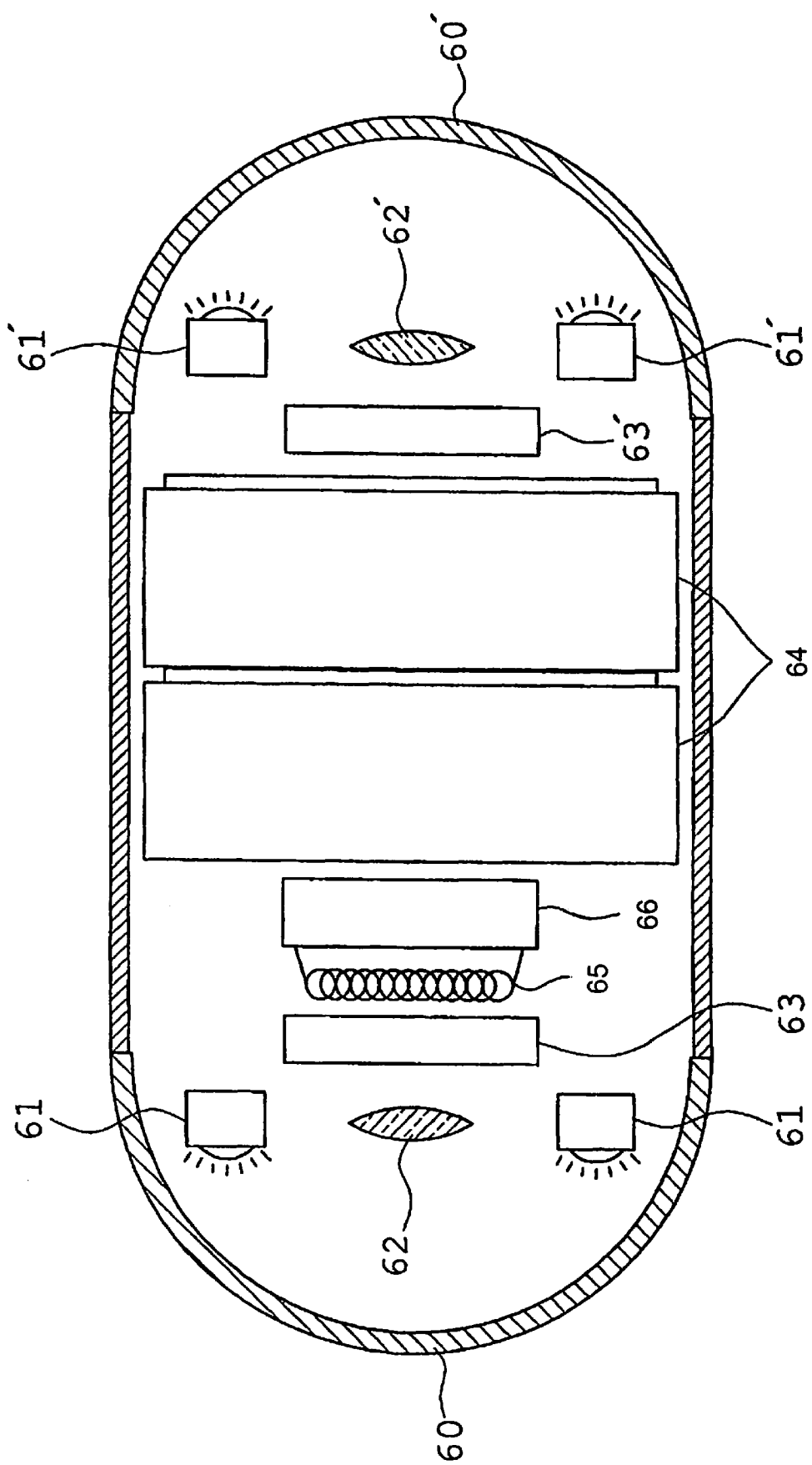
FIG. 22 illustrates the structure of another prior art capsule endoscope.

FIG. 19 is a cross-sectional view along the optical axis showing the optical structure from the transparent cover to the image pickup device of the capsule endoscope of Embodiment 6. FIG. 20 is an enlarged view of an objective optical system and image pickup device shown in FIG. 19. For convenience of illustration, only one objective optical system is illustrated. The optical axis O of the objective optical system is indicated by a single-dashed line in FIGS. 19 and 20 and the central axis of the transparent cover is denoted as C' in FIG. 19.

In the capsule endoscope of Embodiment 6, the objective optical system 2a, the reflecting prism 5a, and the image pickup device are provided completely off the central axis of the dome-shaped transparent cover 4a, which coincides with the central axis of the capsule endoscope. In FIGS. 19 and 20, S is an aperture diaphragm, CG is a cover glass for protecting the image pickup surface of the image pickup device, and IM is the image pickup surface of the image pickup device.

The objective optical system 2a includes, from the object side, a plano-concave lens element 2aL1, a transparent plate 2aL2 with a planar surface on each side, an aperture diaphragm S, and a biconvex lens element 2aL3. In Embodiment 6, the transparent plate 2aL2 is inserted in the optical path of the objective optical system 2a in order to extend the optical path of the objective optical system in the capsule insertion direction. In this way, a large open space can be created on the side of the central axis of the transparent cover 4a opposite from the objective optical system 2a and the image pickup device so that an electrical circuit for controlling the emission of the illuminators can be arranged immediately behind an illuminator, and image processing, memory and communication circuits, and even batteries, (all not illustrated in FIGS. 19 and 20) can be efficiently placed near the image pickup device.

The reflecting prism 5a arranged between the objective optical system 2a and the image pickup surface IM of the image pickup device has a first (entrance) surface 5a1 that is planar, a reflecting second surface 5a2 that is planar, and a third surface 5a3 that is planar. The reflecting prism 5a is arranged so that the optical axis of the objective optical system 2a and the image pickup surface of the image pickup device form an angle Tw of sixty degrees. Light from the objective optical system 2a enters the reflecting prism 5a via first surface 5a1, is reflected toward the image pickup surface IM of the image pickup device by the second surface 5a2, and exits the reflecting prism 5a via the third surface 5a3.

The image pickup device of the capsule endoscope of Embodiment 6 is placed with the image pickup surface IM facing the outside of the capsule endoscope rather than facing the central axis of the capsule endoscope.

Tables 11 and 12 below list the design data and eccentric data of the transparent cover, the objective optical system, and the reflecting prism of the capsule endoscope of Embodiment 6.

TABLE 11

| Surface # | radius of curvature r | surface distance d | refractive index Nd | Abbe No. vd |
|---|---|---|---|---|
| 1 | 5.5000 | 1.0000 | 1.51825 | 64.14 |
| 2 | 4.8000 | 3.5000 | 1.0 | |
| 3 | ∞ | 0.5000 | 1.51825 | 64.14 |
| 4 | 1.1000 | 0.4000 | 1.0 | |
| 5 | ∞ | 2.1000 | 1.51825 | 64.14 |
| 6 | ∞ | 0.1000 | 1.0 | |
| 7 | ∞ (aperture diaphragm) | 0.1000 | 1.0 | |
| 8 | 1.3000 | 0.7000 | 1.51825 | 64.14 |
| 9 | −1.3000 | 0.2000 | 1.0 | |
| 10 | ∞ | 1.0000 | 1.51825 | 64.14 |
| 11 | ∞ | 1.7000 | 1.51825 | 64.14 |
| 12 | ∞ | 0.2000 | 1.51825 | 64.14 |
| 13 | ∞ | 0.0 | 1.0 | |
| 14 | ∞ (image pickup surface) | | | |

TABLE 12

| Surface # | x (mm) | y (mm) | z (mm) | α (°) | β (°) | γ (°) |
|---|---|---|---|---|---|---|
| 3 | 0.0 | −3.0 | 0.0 | 0.0 | 0.0 | 0.0 |
| 11 | 0.0 | 0.0 | 0.0 | 60.0 | 0.0 | 0.0 |
| 12 | 0.0 | 0.0 | 0.0 | −30.0 | 0.0 | 0.0 |

The invention being thus described, it will be obvious that the same may be varied in many ways. Such variations are not to be regarded as a departure from the spirit and scope of the invention. Rather, the scope of the invention shall be defined as set forth in the following claims and their legal equivalents. All such modifications as would be obvious to one skilled in the art are intended to be included within the scope of the following claims.

What is claimed is:

1. A capsule endoscope having a capsule insertion direction along a central axis of the capsule endoscope, the capsule endoscope comprising:
    a first objective optical system that forms on an image surface an image of an object that is viewed by the capsule endoscope in the capsule insertion direction; and
    a second objective optical system that forms on an image surface an image of an object that is viewed by the capsule endoscope in the direction opposite to the capsule insertion direction;
    an image pickup device that has an image pickup surface in the shape of a rectangle having sides Lb and Lc;
    a first reflecting prism that receives light from the first objective optical system and directs it to the image pickup device;
    a second reflecting prism that receives light from the second objective optical system and directs it to the image pickup device;
wherein
    the image pickup device is arranged within the capsule endoscope so that the longer side of the rectangle is in the capsule insertion direction;
    the two image surfaces are in the same plane or are very nearly in the same plane; and
    the following condition is satisfied:

$$La < Lb < Lc$$

where
    La is the width, as measured in a direction parallel to Lb, of the entrance surface of each of the first reflective prism and the second reflective prism;
    Lb is the length of the shorter side of the rectangle defined by the image pickup surface; and
    Lc is the length of the longer side of the rectangle defined by the image pickup surface.

2. The capsule endoscope according to claim 1, and further comprising an image pickup device, wherein said image pickup device captures the two images on an image pickup surface that is situated at, or very nearly at, said two image surfaces.

3. The capsule endoscope according to claim 2, wherein:
    each of the first and second objective optical systems includes a deflector; and
    each of the deflectors folds one of each of the optical axes defined by light entering each of the first and second objective optical systems so that light exiting each of the first and second objective optical systems and forming one of the two images is incident on an image pickup area of said image pickup surface that is different from the image pickup area of the image pickup surface where light forming the other of the two images is incident.

4. The capsule endoscope according to claim 3, wherein each of the deflectors is a respective prism that includes a reflecting surface that folds the optical axis of light that enters a respective one of the first and second objective optical systems.

5. The capsule endoscope according to claim 2, and further comprising a deflector, wherein the deflector deflects the optical axis of each of said first objective optical system and said second objective optical system so that the light forming one of the two images is incident on an image pickup area of said image pickup surface that is different from the image pickup area of the image pickup surface where light forming the other of the two images is incident.

6. The capsule endoscope according to claim 2, wherein a plane defined by the image pickup surface is parallel to the capsule insertion direction.

7. The capsule endoscope according to claim 6, wherein:
said image pickup surface faces the opposite direction to facing said central axis.

8. A capsule endoscope having a capsule insertion direction along a central axis of the capsule endoscope, wherein an image of an object in the capsule insertion direction and an image of an object in the direction opposite to the capsule insertion direction are acquired in different image pickup areas of one image pickup device, and further comprising an image pickup unit for acquiring the two images from opposite directions, the image pickup unit including:
two objective optical systems, each of which includes an object-side lens element;
an image pickup device that includes an image pickup surface; and
a deflector between the object-side lens element of each objective optical system and the image pickup surface for deflecting the optical axes of light forming images on the image pickup surface, with each deflector being a reflecting prism having an entrance surface;

wherein
the image pickup device is arranged completely off the central axis of the capsule endoscope; and
the following condition is satisfied:

$$La < Lb < Lc$$

where
$La$ is the width, as measured in a direction parallel to $Lb$, of the entrance surface of each of the reflecting prisms that receive light from respective objective optical systems;
$Lb$ is the length of the shorter side of the rectangle defined by the image pickup surface; and
$Lc$ is the length of the longer side of the rectangle defined by the image pickup surface.

* * * * *